(12) United States Patent
Dwyer et al.

(10) Patent No.: US 8,419,799 B2
(45) Date of Patent: Apr. 16, 2013

(54) ASSEMBLY TOOL FOR MODULAR IMPLANTS AND ASSOCIATED METHOD

(75) Inventors: Kimberly Ann Dwyer, Fort Wayne, IN (US); David Wayne Daniels, Winona Lake, IN (US); Brad Alan Parker, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 1229 days.

(21) Appl. No.: 11/977,138

(22) Filed: Oct. 23, 2007

(65) Prior Publication Data

US 2008/0091212 A1 Apr. 17, 2008

Related U.S. Application Data

(63) Continuation of application No. 10/606,401, filed on Jun. 25, 2003, now Pat. No. 7,297,166.

(51) Int. Cl.
*A61B 17/56* (2006.01)
*A61B 17/88* (2006.01)

(52) U.S. Cl.
USPC ........................................ 623/22.12; 606/99

(58) Field of Classification Search ............... 606/62, 606/63, 65, 66, 68, 99, 102, 104; 623/20.35, 623/20.36, 22.11, 22.12, 22.4, 22.41–22.46, 623/23.15, 23.23, 23.44
See application file for complete search history.

(56) References Cited

U.S. PATENT DOCUMENTS

| | | |
|---|---|---|
| 650,795 A | 5/1900 | Maxwell et al. |
| 1,029,402 A | 6/1912 | Ritter |
| 1,383,304 A | 7/1921 | Hughes et al. |
| 1,423,649 A | 7/1922 | Daniel |
| 1,534,692 A | 4/1925 | Davis |
| 2,631,584 A | 3/1953 | Purificato |
| 2,661,033 A | 12/1953 | Daniel |
| 2,711,196 A | 6/1955 | Daniel |
| 2,834,382 A | 5/1958 | Daniel |
| 2,856,637 A | 10/1958 | Daniel |

(Continued)

FOREIGN PATENT DOCUMENTS

| | | |
|---|---|---|
| DE | 3538654 A1 | 4/1987 |
| EP | 0206777 A2 | 12/1986 |

(Continued)

OTHER PUBLICATIONS

European Search Report corresponding to European patent application EP 08 16 7776, dated Feb. 11, 2010 (5 pages).

(Continued)

*Primary Examiner* — Eduardo C Robert
*Assistant Examiner* — David Comstock
(74) *Attorney, Agent, or Firm* — Maginot, Moore & Beck, LLP

(57) ABSTRACT

An assembly tool (1) for assembly of a first component (2) of a prosthesis (4) to a second component (6) of the prosthesis (4) for use in joint arthroplasty is provided. The tool (1) includes a first member (8) operably associated with the first component (2). The first member (8) defines a first member longitudinal axis (10) of the first member (8). The tool also includes a second member (12) operably associated with the second component (6). The second member (12) defines a second member longitudinal axis (14) of the second member (12). The second member (12) is adapted to provide relative motion of the second member (12) with respect to the first member (8) when the second member (12) is rotated relative to the first member (8) about the second member longitudinal axis (14).

27 Claims, 28 Drawing Sheets

U.S. PATENT DOCUMENTS

| | | |
|---|---|---|
| 2,864,282 A | 12/1958 | Daniel |
| 2,877,936 A | 3/1959 | Michel |
| 2,895,154 A | 7/1959 | Belcher |
| 2,902,596 A | 9/1959 | Rockwell et al. |
| 2,914,224 A | 11/1959 | Michel |
| 2,944,373 A | 7/1960 | Mentley et al. |
| 2,955,905 A | 10/1960 | Davies et al. |
| 2,957,610 A | 10/1960 | Michel |
| 2,974,699 A | 3/1961 | Boles et al. |
| 2,975,944 A | 3/1961 | Michel |
| 2,977,726 A | 4/1961 | Daniel |
| 2,981,035 A | 4/1961 | Mentley et al. |
| 2,994,461 A | 8/1961 | Michel |
| 2,994,988 A | 8/1961 | Mentley et al. |
| 3,048,307 A | 8/1962 | Michel |
| 3,059,278 A | 10/1962 | Daniel |
| 3,071,862 A | 1/1963 | Daniel et al. |
| 3,077,877 A | 2/1963 | Daniel et al. |
| 3,092,934 A | 6/1963 | Daniel |
| 3,092,935 A | 6/1963 | Daniel |
| 3,101,875 A | 8/1963 | Michel |
| 3,135,136 A | 6/1964 | Mentley et al. |
| 3,177,507 A | 4/1965 | Becker et al. |
| 3,180,532 A | 4/1965 | Michel |
| 3,220,311 A | 11/1965 | Anthony et al. |
| 3,250,745 A | 5/1966 | Davis et al. |
| 3,293,987 A | 12/1966 | Daniel |
| 3,300,833 A | 1/1967 | Daniel |
| 3,301,134 A | 1/1967 | Daniel |
| 3,319,526 A | 5/1967 | Daniel et al. |
| 3,331,115 A | 7/1967 | Daniel |
| 3,335,639 A | 8/1967 | Daniel |
| 3,424,783 A | 1/1969 | Harper et al. |
| 3,443,478 A | 5/1969 | Daniel |
| 3,451,111 A | 6/1969 | Daniel |
| 3,479,387 A | 11/1969 | Daniels et al. |
| 3,479,388 A | 11/1969 | Daniels |
| 3,483,175 A | 12/1969 | Harper et al. |
| 3,494,752 A | 2/1970 | Daniel |
| 3,499,920 A | 3/1970 | Daniels |
| 3,541,868 A | 11/1970 | Hall |
| 3,580,027 A | 5/1971 | Daniel et al. |
| 3,580,029 A | 5/1971 | Daniel et al. |
| 3,604,235 A | 9/1971 | Motz et al. |
| 3,629,981 A | 12/1971 | McCaffery |
| 3,631,703 A | 1/1972 | Bregi et al. |
| 3,633,583 A | 1/1972 | Fishbein |
| 3,668,139 A | 6/1972 | Daniels et al. |
| 3,673,887 A | 7/1972 | Daniel et al. |
| 3,679,728 A | 7/1972 | Morgan et al. |
| 3,679,729 A | 7/1972 | Daniels |
| 3,691,718 A | 9/1972 | Woodruff et al. |
| 3,700,957 A | 10/1972 | Daniels |
| 3,705,513 A | 12/1972 | Daniel |
| 3,754,586 A | 8/1973 | Daniels |
| 3,810,312 A | 5/1974 | Carson |
| 3,849,322 A | 11/1974 | Wendler et al. |
| 3,869,394 A | 3/1975 | Daniels et al. |
| 3,889,558 A | 6/1975 | Duncan |
| 3,912,727 A | 10/1975 | Daniels |
| 4,004,581 A | 1/1977 | Heimke et al. |
| 4,009,712 A | 3/1977 | Burstein et al. |
| 4,035,988 A | 7/1977 | Daniels |
| 4,051,559 A | 10/1977 | Pifferi |
| D246,507 S | 11/1977 | Danielson |
| 4,115,875 A | 9/1978 | Rambert et al. |
| 4,116,200 A | 9/1978 | Braun et al. |
| 4,150,909 A | 4/1979 | Hibarger et al. |
| D257,533 S | 11/1980 | Bevilacqua et al. |
| D258,957 S | 4/1981 | Bevilacqua et al. |
| 4,305,394 A | 12/1981 | Bertuch, Jr. |
| D266,768 S | 11/1982 | Bevilacqua et al. |
| D267,151 S | 12/1982 | Bruce et al. |
| 4,398,074 A | 8/1983 | Danielson et al. |
| D275,006 S | 8/1984 | Danielson et al. |
| 4,473,070 A | 9/1984 | Matthews et al. |
| D282,246 S | 1/1986 | Thomas et al. |
| D282,350 S | 1/1986 | Thomas et al. |
| 4,601,289 A | 7/1986 | Chiarizzio et al. |
| D285,073 S | 8/1986 | Danielson et al. |
| D285,198 S | 8/1986 | Danielson et al. |
| 4,608,055 A | 8/1986 | Morrey et al. |
| D286,198 S | 10/1986 | Bancroft |
| D286,285 S | 10/1986 | Danielson et al. |
| D287,494 S | 12/1986 | Danielson et al. |
| D289,155 S | 4/1987 | Brooks et al. |
| 4,658,808 A | 4/1987 | Link |
| D290,399 S | 6/1987 | Kitchens |
| 4,670,015 A | 6/1987 | Freeman |
| 4,686,971 A | 8/1987 | Harris et al. |
| 4,710,946 A | 12/1987 | Hinch et al. |
| 4,716,894 A | 1/1988 | Lazzeri et al. |
| 4,738,256 A | 4/1988 | Freeman et al. |
| 4,777,942 A | 10/1988 | Frey et al. |
| D303,114 S | 8/1989 | Danielson et al. |
| D304,587 S | 11/1989 | Danielson et al. |
| 4,891,545 A | 1/1990 | Capek et al. |
| 4,917,530 A | 4/1990 | Engelhardt et al. |
| 4,923,422 A | 5/1990 | Capek et al. |
| 4,938,773 A | 7/1990 | Strand |
| 4,959,066 A | 9/1990 | Dunn et al. |
| 4,969,911 A | 11/1990 | Greene |
| D313,233 S | 12/1990 | Andrews, Sr. et al. |
| D315,343 S | 3/1991 | Andrews et al. |
| 4,997,621 A | 3/1991 | Johansson et al. |
| 5,002,578 A | 3/1991 | Luman |
| 5,002,581 A | 3/1991 | Paxson et al. |
| 5,015,255 A | 5/1991 | Kuslich |
| 5,020,519 A | 6/1991 | Hayes et al. |
| D318,051 S | 7/1991 | Danielson et al. |
| D319,439 S | 8/1991 | Danielson et al. |
| 5,047,033 A | 9/1991 | Fallin |
| 5,049,150 A | 9/1991 | Cozad |
| D320,985 S | 10/1991 | Danielson et al. |
| 5,053,037 A | 10/1991 | Lackey |
| 5,060,505 A | 10/1991 | Tury et al. |
| 5,080,685 A | 1/1992 | Bolesky et al. |
| D323,657 S | 2/1992 | Danielson et al. |
| 5,099,714 A | 3/1992 | Hutchison et al. |
| 5,100,407 A | 3/1992 | Conrad et al. |
| 5,108,452 A | 4/1992 | Fallin et al. |
| 5,133,588 A | 7/1992 | Hutchison et al. |
| 5,135,529 A | 8/1992 | Paxson et al. |
| 5,162,626 A | 11/1992 | Hutchison et al. |
| 5,171,055 A | 12/1992 | Hutchison et al. |
| 5,171,244 A | 12/1992 | Caspari et al. |
| 5,181,928 A | 1/1993 | Bolesky et al. |
| 5,184,017 A | 2/1993 | Tury et al. |
| 5,192,283 A | 3/1993 | Ling et al. |
| 5,197,989 A | 3/1993 | Hinckfuss et al. |
| 5,201,882 A | 4/1993 | Paxson |
| 5,207,680 A | 5/1993 | Dietz et al. |
| 5,218,814 A | 6/1993 | Teal et al. |
| D337,639 S | 7/1993 | Beckman |
| 5,228,459 A | 7/1993 | Caspari et al. |
| D338,473 S | 8/1993 | Patterson et al. |
| 5,238,267 A | 8/1993 | Hutchison et al. |
| 5,247,171 A | 9/1993 | Wlodarczyk et al. |
| D340,461 S | 10/1993 | Patterson et al. |
| 5,263,498 A | 11/1993 | Caspari et al. |
| 5,290,313 A | 3/1994 | Heldreth |
| 5,304,181 A | 4/1994 | Caspari et al. |
| D346,979 S | 5/1994 | Stalcup et al. |
| 5,331,124 A | 7/1994 | Danielson |
| 5,336,226 A | 8/1994 | McDaniel et al. |
| 5,342,363 A | 8/1994 | Richelsoph |
| 5,344,423 A | 9/1994 | Dietz et al. |
| 5,345,483 A | 9/1994 | Johansson et al. |
| 5,352,231 A | 10/1994 | Brumfield et al. |
| D352,521 S | 11/1994 | Sculler et al. |
| D353,394 S | 12/1994 | Stefanski et al. |
| 5,370,706 A | 12/1994 | Bolesky et al. |
| 5,372,209 A | 12/1994 | Raihert et al. |
| D355,186 S | 2/1995 | Danielson et al. |
| D355,187 S | 2/1995 | Danielson et al. |
| 5,387,218 A | 2/1995 | Meswania |
| 5,395,376 A | 3/1995 | Caspari et al. |

| Patent | Date | Name |
|---|---|---|
| D357,315 S | 4/1995 | Dietz |
| 5,403,320 A | 4/1995 | Luman et al. |
| 5,409,492 A | 4/1995 | Jones et al. |
| 5,415,659 A | 5/1995 | Lee et al. |
| 5,420,910 A | 5/1995 | Rudokas et al. |
| D359,064 S | 6/1995 | Sculler et al. |
| 5,422,478 A | 6/1995 | Wlodarczyk et al. |
| 5,457,100 A | 10/1995 | Daniel |
| 5,459,294 A | 10/1995 | Danielson |
| D364,621 S | 11/1995 | Clarke et al. |
| 5,468,243 A | 11/1995 | Halpern |
| 5,470,336 A | 11/1995 | Ling et al. |
| 5,474,559 A | 12/1995 | Bertin et al. |
| 5,476,466 A | 12/1995 | Barrette et al. |
| D365,824 S | 1/1996 | Danielson et al. |
| 5,486,180 A | 1/1996 | Dietz et al. |
| 5,496,324 A | 3/1996 | Barnes |
| 5,507,815 A | 4/1996 | Wagner et al. |
| 5,507,824 A | 4/1996 | Lennox |
| 5,507,830 A | 4/1996 | DeMane et al. |
| 5,507,833 A | 4/1996 | Bohn |
| 5,527,316 A | 6/1996 | Stone et al. |
| 5,528,640 A | 6/1996 | Johansson et al. |
| 5,534,005 A | 7/1996 | Tokish, Jr. et al. |
| 5,540,694 A | 7/1996 | DeCarlo, Jr. et al. |
| 5,555,551 A | 9/1996 | Rudokas et al. |
| 5,569,255 A | 10/1996 | Burke |
| D376,527 S | 12/1996 | Apolinski et al. |
| 5,591,233 A | 1/1997 | Kelman et al. |
| 5,593,411 A | 1/1997 | Stalcup et al. |
| 5,600,892 A | 2/1997 | Peugh et al. |
| 5,601,563 A | 2/1997 | Burke et al. |
| 5,601,567 A | 2/1997 | Swajger et al. |
| 5,607,269 A | 3/1997 | Dowd et al. |
| 5,607,431 A | 3/1997 | Dudasik et al. |
| D379,578 S | 6/1997 | Daniels |
| 5,643,271 A | 7/1997 | Sederholm et al. |
| 5,645,607 A | 7/1997 | Hickey |
| 5,653,714 A | 8/1997 | Dietz et al. |
| 5,653,764 A | 8/1997 | Murphy |
| 5,653,765 A | 8/1997 | McTighe et al. |
| 5,658,349 A | 8/1997 | Brooks et al. |
| 5,663,993 A | 9/1997 | Danielson et al. |
| 5,669,812 A | 9/1997 | Schockemoehl et al. |
| 5,683,395 A | 11/1997 | Mikhail |
| D387,962 S | 12/1997 | Apolinski et al. |
| D387,963 S | 12/1997 | Clark |
| 5,697,932 A | 12/1997 | Smith et al. |
| 5,702,480 A | 12/1997 | Kropf et al. |
| 5,702,487 A | 12/1997 | Averill et al. |
| 5,715,672 A | 2/1998 | Schockemoehl et al. |
| D392,534 S | 3/1998 | Degen et al. |
| D392,866 S | 3/1998 | Degen et al. |
| 5,725,592 A | 3/1998 | White et al. |
| 5,728,128 A | 3/1998 | Crickenberger et al. |
| 5,735,857 A | 4/1998 | Lane |
| 5,743,915 A | 4/1998 | Bertin et al. |
| 5,752,972 A | 5/1998 | Hoogeboom |
| 5,755,803 A | 5/1998 | Haines et al. |
| 5,766,261 A | 6/1998 | Neal et al. |
| 5,769,855 A | 6/1998 | Bertin et al. |
| 5,776,200 A | 7/1998 | Johnson et al. |
| 5,782,921 A | 7/1998 | Colleran et al. |
| 5,792,143 A | 8/1998 | Samuelson et al. |
| 5,804,886 A | 9/1998 | Danielson et al. |
| 5,810,827 A | 9/1998 | Haines et al. |
| 5,810,829 A | 9/1998 | Elliott et al. |
| 5,810,830 A | 9/1998 | Noble et al. |
| 5,824,097 A | 10/1998 | Gabriel et al. |
| 5,849,015 A | 12/1998 | Haywood et al. |
| 5,850,162 A | 12/1998 | Danielsons |
| 5,853,415 A | 12/1998 | Bertin et al. |
| 5,858,020 A | 1/1999 | Johnson et al. |
| 5,858,828 A | 1/1999 | Seliskar et al. |
| 5,860,969 A | 1/1999 | White et al. |
| 5,860,981 A | 1/1999 | Bertin et al. |
| 5,876,459 A | 3/1999 | Powell |
| 5,879,354 A | 3/1999 | Haines et al. |
| 5,879,391 A | 3/1999 | Slamin |
| 5,902,340 A | 5/1999 | White et al. |
| 5,906,644 A | 5/1999 | Powell |
| 5,908,423 A | 6/1999 | Kashuba et al. |
| 5,919,195 A | 7/1999 | Wilson et al. |
| 5,923,422 A | 7/1999 | Keens et al. |
| 5,935,172 A | 8/1999 | Ochoa et al. |
| 5,950,121 A | 9/1999 | Kaminsky et al. |
| 5,951,606 A | 9/1999 | Burke |
| 5,954,460 A | 9/1999 | Degen et al. |
| 5,957,768 A | 9/1999 | Schockemoehl et al. |
| 5,957,925 A | 9/1999 | Cook et al. |
| 5,966,599 A | 10/1999 | Walker et al. |
| 5,968,049 A | 10/1999 | Da Rold |
| 5,973,064 A | 10/1999 | Zhao et al. |
| 5,976,145 A | 11/1999 | Kennefick, III |
| 5,976,147 A | 11/1999 | LaSalle et al. |
| 5,976,188 A | 11/1999 | Dextradeur et al. |
| 5,993,455 A | 11/1999 | Noble |
| 5,996,812 A | 12/1999 | Sokol, Jr. |
| 5,997,419 A | 12/1999 | Daniels et al. |
| 6,045,556 A | 4/2000 | Cohen |
| 6,048,365 A | 4/2000 | Burrows et al. |
| 6,054,895 A | 4/2000 | Danielsons et al. |
| 6,056,084 A | 5/2000 | Schockemoehl et al. |
| 6,056,754 A | 5/2000 | Haines et al. |
| 6,058,301 A | 5/2000 | Daniels |
| 6,059,528 A | 5/2000 | Danielson et al. |
| 6,063,123 A | 5/2000 | Burrows et al. |
| 6,069,048 A | 5/2000 | Daniel |
| 6,071,311 A | 6/2000 | O'Neil et al. |
| 6,077,783 A | 6/2000 | Allman et al. |
| 6,080,162 A | 6/2000 | Dye et al. |
| 6,090,146 A | 7/2000 | Rozow, III et al. |
| 6,096,625 A | 8/2000 | Daniels et al. |
| 6,117,138 A | 9/2000 | Burrows et al. |
| 6,120,507 A | 9/2000 | Allard et al. |
| 6,121,147 A | 9/2000 | Daniel et al. |
| 6,126,694 A | 10/2000 | Gray, Jr. |
| 6,139,581 A | 10/2000 | Engh et al. |
| 6,159,214 A | 12/2000 | Michelson |
| 6,162,226 A | 12/2000 | DeCarlo, Jr. et al. |
| 6,165,177 A | 12/2000 | Wilson et al. |
| 6,179,116 B1 | 1/2001 | Noniewicz et al. |
| 6,179,877 B1 | 1/2001 | Burke |
| 6,181,925 B1 | 1/2001 | Kaminsky et al. |
| 6,185,416 B1 | 2/2001 | Rudokas et al. |
| 6,193,759 B1 | 2/2001 | Ro et al. |
| 6,197,064 B1 | 3/2001 | Haines et al. |
| 6,197,065 B1 | 3/2001 | Martin et al. |
| 6,201,253 B1 | 3/2001 | Allman et al. |
| 6,206,884 B1 | 3/2001 | Masini |
| 6,219,538 B1 | 4/2001 | Kaminsky et al. |
| 6,224,605 B1 | 5/2001 | Anderson et al. |
| 6,232,721 B1 | 5/2001 | Danielsons |
| 6,235,590 B1 | 5/2001 | Daniel et al. |
| 6,238,435 B1 | 5/2001 | Meulink et al. |
| D443,882 S | 6/2001 | Daniels et al. |
| 6,241,847 B1 | 6/2001 | Allman et al. |
| 6,242,978 B1 | 6/2001 | Danielsons |
| 6,258,093 B1 | 7/2001 | Edwards et al. |
| 6,258,095 B1 | 7/2001 | Lombardo et al. |
| 6,258,097 B1 | 7/2001 | Cook et al. |
| 6,260,279 B1 | 7/2001 | Apolinski et al. |
| 6,263,998 B1 | 7/2001 | Schockemoehl et al. |
| 6,264,699 B1 | 7/2001 | Noiles et al. |
| 6,270,502 B1 | 8/2001 | Stulberg |
| 6,281,935 B1 | 8/2001 | Twitchell et al. |
| 6,285,871 B1 | 9/2001 | Daniels |
| 6,287,342 B1 | 9/2001 | Copf et al. |
| 6,310,410 B1 | 10/2001 | Lin et al. |
| D450,304 S | 11/2001 | Daniels et al. |
| 6,316,817 B1 | 11/2001 | Seliskar et al. |
| 6,318,651 B1 | 11/2001 | Spiering |
| 6,319,286 B1 | 11/2001 | Fernandez et al. |
| 6,330,845 B1 | 12/2001 | Meulink |
| 6,332,886 B1 | 12/2001 | Green et al. |
| 6,335,766 B1 | 1/2002 | Twitchell et al. |
| 6,354,908 B2 | 3/2002 | Allman et al. |
| 6,355,068 B1 | 3/2002 | Doubler et al. |

| | | |
|---|---|---|
| 6,355,532 B1 | 3/2002 | Seliskar et al. |
| 6,361,563 B2 | 3/2002 | Terrill-Grisoni et al. |
| 6,366,422 B1 | 4/2002 | Daniel et al. |
| 6,372,520 B1 | 4/2002 | Hsia et al. |
| D457,176 S | 5/2002 | Daniels et al. |
| 6,382,276 B1 | 5/2002 | Daniels et al. |
| D458,947 S | 6/2002 | Svetlik et al. |
| 6,400,415 B1 | 6/2002 | Danielsons |
| 6,406,217 B1 | 6/2002 | Daniel et al. |
| 6,419,147 B1 | 7/2002 | Daniel |
| 6,422,562 B1 | 7/2002 | Daniel |
| 6,422,816 B1 | 7/2002 | Danielson |
| 6,428,578 B2 | 8/2002 | White |
| 6,432,110 B1 | 8/2002 | Richelsoph |
| 6,432,141 B1 | 8/2002 | Stocks et al. |
| 6,440,139 B2 | 8/2002 | Michelson |
| D467,485 S | 12/2002 | Daniels et al. |
| 6,488,713 B1 | 12/2002 | Hershberger |
| D468,180 S | 1/2003 | Bruno et al. |
| 6,505,684 B2 | 1/2003 | Rayssiguier et al. |
| 6,508,841 B1 | 1/2003 | Martin et al. |
| D469,671 S | 2/2003 | Prell et al. |
| 6,517,581 B2 | 2/2003 | Blarney |
| RE38,058 E | 4/2003 | Fallin |
| 6,565,029 B2 | 5/2003 | Zweighaft et al. |
| 6,568,618 B1 | 5/2003 | Vanderheyden et al. |
| 6,589,284 B1 | 7/2003 | Silberer |
| 6,589,285 B2 | 7/2003 | Penenberg |
| 6,600,516 B1 | 7/2003 | Danielsons et al. |
| 6,609,900 B2 | 8/2003 | Lucke et al. |
| 6,663,616 B1 | 12/2003 | Roth et al. |
| 6,676,706 B1 | 1/2004 | Mears et al. |
| 6,682,568 B2 | 1/2004 | Despres, III et al. |
| 6,692,530 B2 | 2/2004 | Doubler et al. |
| 6,700,359 B2 | 3/2004 | Daniels et al. |
| 6,702,854 B1 | 3/2004 | Cheal et al. |
| 6,706,072 B2 | 3/2004 | Dwyer et al. |
| 6,706,621 B2 | 3/2004 | Cox et al. |
| 6,723,129 B2 | 4/2004 | Dwyer et al. |
| 6,740,090 B1 | 5/2004 | Cragg et al. |
| 6,743,235 B2 | 6/2004 | Subba Rao |
| 6,744,243 B2 | 6/2004 | Daniels et al. |
| 6,751,266 B1 | 6/2004 | Danielsons |
| 6,770,100 B2 | 8/2004 | Draenert |
| D497,499 S | 10/2004 | Daniel et al. |
| 6,811,376 B2 | 11/2004 | Arel et al. |
| 6,812,792 B2 | 11/2004 | Mattsson et al. |
| 6,824,552 B2 | 11/2004 | Robison et al. |
| 6,846,314 B2 | 1/2005 | Shapira |
| 6,856,029 B1 | 2/2005 | Daniel et al. |
| 6,870,160 B1 | 3/2005 | Daniel |
| 6,875,218 B2 | 4/2005 | Dye et al. |
| 6,883,217 B2 | 4/2005 | Barrette et al. |
| D505,611 S | 5/2005 | Daniel et al. |
| 6,905,515 B1 | 6/2005 | Gilbertson |
| 6,911,048 B2 | 6/2005 | Fernandez et al. |
| 6,949,101 B2 | 9/2005 | McCleary et al. |
| 6,990,691 B2 | 1/2006 | Klotz et al. |
| 7,001,392 B2 | 2/2006 | McGovern |
| 7,008,420 B2 | 3/2006 | Okada |
| 7,022,141 B2 | 4/2006 | Dwyer et al. |
| 7,074,224 B2 | 7/2006 | Daniels et al. |
| 7,641,658 B2 | 1/2010 | Shaolian et al. |
| 2001/0001121 A1 | 5/2001 | Lombardo et al. |
| 2001/0007957 A1 | 7/2001 | Martin et al. |
| 2001/0016779 A1 | 8/2001 | Lubinus |
| 2001/0021622 A1 | 9/2001 | Allman et al. |
| 2001/0034526 A1 | 10/2001 | Kuslich et al. |
| 2002/0043296 A1 | 4/2002 | Daniels et al. |
| 2002/0058999 A1 | 5/2002 | Dwyer et al. |
| 2002/0059000 A1 | 5/2002 | Dwyer et al. |
| 2002/0127115 A1 | 9/2002 | Lucke et al. |
| 2002/0183758 A1 | 12/2002 | Middleton et al. |
| 2002/0195512 A1 | 12/2002 | Zweighft et al. |
| 2003/0001551 A1 | 1/2003 | Daniels et al. |
| 2003/0048003 A1 | 3/2003 | Daniels et al. |
| 2003/0050645 A1 | 3/2003 | Parker et al. |
| 2003/0071329 A1 | 4/2003 | Cox et al. |
| 2003/0093080 A1 | 5/2003 | Brown et al. |
| 2003/0095368 A1 | 5/2003 | Daniels et al. |
| 2003/0109882 A1 | 6/2003 | Shirado et al. |
| 2003/0114933 A1 | 6/2003 | Bouttens et al. |
| 2003/0130740 A1 | 7/2003 | Stocks et al. |
| 2003/0171756 A1 | 9/2003 | Fallin et al. |
| 2003/0171816 A1 | 9/2003 | Scifert et al. |
| 2003/0180146 A1 | 9/2003 | Arel et al. |
| 2003/0187449 A1 | 10/2003 | McCleary et al. |
| 2003/0204269 A1 | 10/2003 | Gerbec et al. |
| 2003/0220698 A1 | 11/2003 | Mears et al. |
| 2003/0228033 A1 | 12/2003 | Daniel et al. |
| 2004/0015239 A1 | 1/2004 | Beguec |
| 2004/0017085 A1 | 1/2004 | Daniels |
| 2004/0054419 A1 | 3/2004 | Serra et al. |
| 2004/0058997 A1 | 3/2004 | Daniel |
| 2004/0064186 A1 | 4/2004 | McCleary et al. |
| 2004/0066217 A1 | 4/2004 | Daniels et al. |
| 2004/0092951 A1 | 5/2004 | Serra et al. |
| 2004/0122437 A1 | 6/2004 | Dwyer et al. |
| 2004/0122439 A1 | 6/2004 | Dwyer et al. |
| 2004/0122440 A1 | 6/2004 | Daniels et al. |
| 2004/0122525 A1 | 6/2004 | Daniels et al. |
| 2004/0130394 A1 | 7/2004 | Mattsson et al. |
| 2004/0135233 A1 | 7/2004 | Cox et al. |
| 2004/0147933 A1 | 7/2004 | McGovern et al. |
| 2004/0172138 A1 | 9/2004 | May et al. |
| 2004/0172139 A1 | 9/2004 | Dwyer et al. |
| 2004/0210471 A1 | 10/2004 | Luby et al. |
| 2004/0267266 A1 | 12/2004 | Daniels et al. |
| 2004/0267267 A1 | 12/2004 | Daniels et al. |
| 2004/0267372 A1 | 12/2004 | Vanasse et al. |
| 2004/0267373 A1 | 12/2004 | Dwyer et al. |
| 2005/0004679 A1 | 1/2005 | Sederholm et al. |
| 2005/0010992 A1 | 1/2005 | Klotz et al. |
| 2005/0015049 A1 | 1/2005 | Rioux et al. |
| 2005/0033444 A1 | 2/2005 | Jones et al. |
| 2005/0057239 A1 | 3/2005 | Fowler et al. |
| 2005/0078289 A1 | 4/2005 | Daniel et al. |
| 2005/0081910 A1 | 4/2005 | Danielson et al. |
| 2005/0115391 A1 | 6/2005 | Baker et al. |
| 2005/0154331 A1 | 7/2005 | Christie et al. |
| 2005/0188878 A1 | 9/2005 | Baker et al. |
| 2005/0209597 A1 | 9/2005 | Long et al. |
| 2005/0222572 A1 | 10/2005 | Chana |
| 2005/0234461 A1 | 10/2005 | Burdulis et al. |
| 2005/0234559 A1 | 10/2005 | Fernandez et al. |
| 2005/0267937 A1 | 12/2005 | Daniels et al. |
| 2005/0288676 A1 | 12/2005 | Schneiders et al. |
| 2006/0015110 A1 | 1/2006 | Pepper |
| 2006/0058810 A1 | 3/2006 | Wozencroft et al. |
| 2006/0217737 A1 | 9/2006 | Iversen |

FOREIGN PATENT DOCUMENTS

| | | | |
|---|---|---|---|
| EP | 0511244 A1 | 11/1992 | |
| EP | 0595956 A1 | 5/1994 | |
| EP | 0661023 A2 | 7/1995 | |
| EP | 0726063 A1 | 8/1996 | |
| EP | 0728449 | 8/1996 | |
| EP | 0842639 A2 | 5/1998 | |
| EP | 0861635 A2 | 9/1998 | |
| EP | 1 080 701 | 3/2001 | |
| EP | 1080701 A2 | 3/2001 | |
| EP | 1084680 A2 | 3/2001 | |
| EP | 1080701 A3 | 7/2001 | |
| EP | 1201191 A1 | 5/2002 | |
| EP | 1263334 A2 | 12/2002 | |
| EP | 1323395 A2 | 7/2003 | |
| EP | 1348384 A2 | 10/2003 | |
| EP | 1369089 A2 | 12/2003 | |
| EP | 1493407 A2 | 1/2005 | |
| EP | 1493407 A3 | 4/2005 | |
| EP | 1191906 | 6/2005 | |
| EP | 1591084 A1 | 11/2005 | |
| EP | 1080701 B1 | 8/2006 | |
| FR | 2699400 A1 | 6/1994 | |
| FR | 2737107 A1 | 1/1997 | |
| FR | 2828397 A1 | 2/2003 | |
| GB | 2250441 A | 6/1992 | |
| JP | 2003339724 A | 12/2003 | |

| | | | |
|---|---|---|---|
| WO | 9110408 A1 | 7/1991 |
| WO | 9210138 A1 | 6/1992 |
| WO | 9301769 A1 | 2/1993 |
| WO | 9412123 A1 | 6/1994 |
| WO | 9427507 A1 | 12/1994 |
| WO | 9615738 A1 | 5/1996 |
| WO | 9615739 A1 | 5/1996 |
| WO | WO 96/15739 | 5/1996 |
| WO | 9815739 A1 | 4/1998 |
| WO | 0167997 | 9/2001 |
| WO | 02102254 A2 | 12/2002 |
| WO | 03015642 A1 | 2/2003 |
| WO | 03065906 A2 | 8/2003 |
| WO | 03082159 A1 | 10/2003 |
| WO | 03092513 A1 | 11/2003 |
| WO | 03094698 A2 | 11/2003 |
| WO | 03094803 A1 | 11/2003 |

OTHER PUBLICATIONS

Zimmer, "Metasul® LDH™ Large Diameter Head," Surgical Technique, available at least as early as Sep. 28, 2006, (19 pages).
Gray, "Clinically-Oriented Geometry of the Femur," Thesis, Aug. 1995, Queen's University, Ontario, Canada (73 pages).
Chinese Office Action corresponding to Chinese patent application 200710185735.6, dated Feb. 11, 2011, 13 pages.
European Search Report corresponding European patent application EP 11 15 1451, dated Feb. 16, 2011, 5 pages.
Paul, H.A., et al. "Development of a Surgical Robot for Cementless Total Hip Arthroplasty," Clinical Orthopedics & Related Research 285 Dec. 1992: 57-66.
Depuy Orthopaedics, Inc., "S-ROM Modular Hip System, Minimally Invasive Calcar Miller Surgical Technique," 0612-04-503, 2004, Depuy Orthopaedics, Inc.

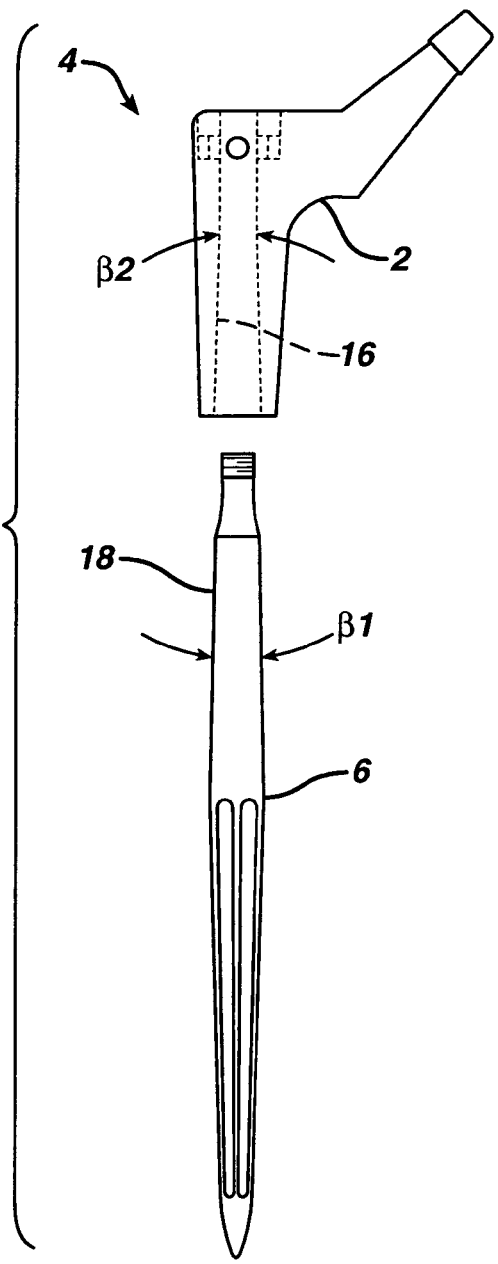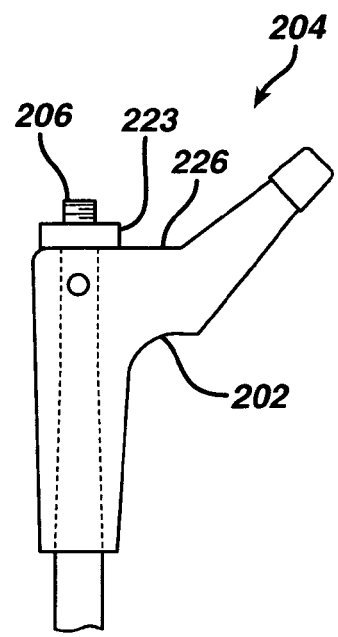

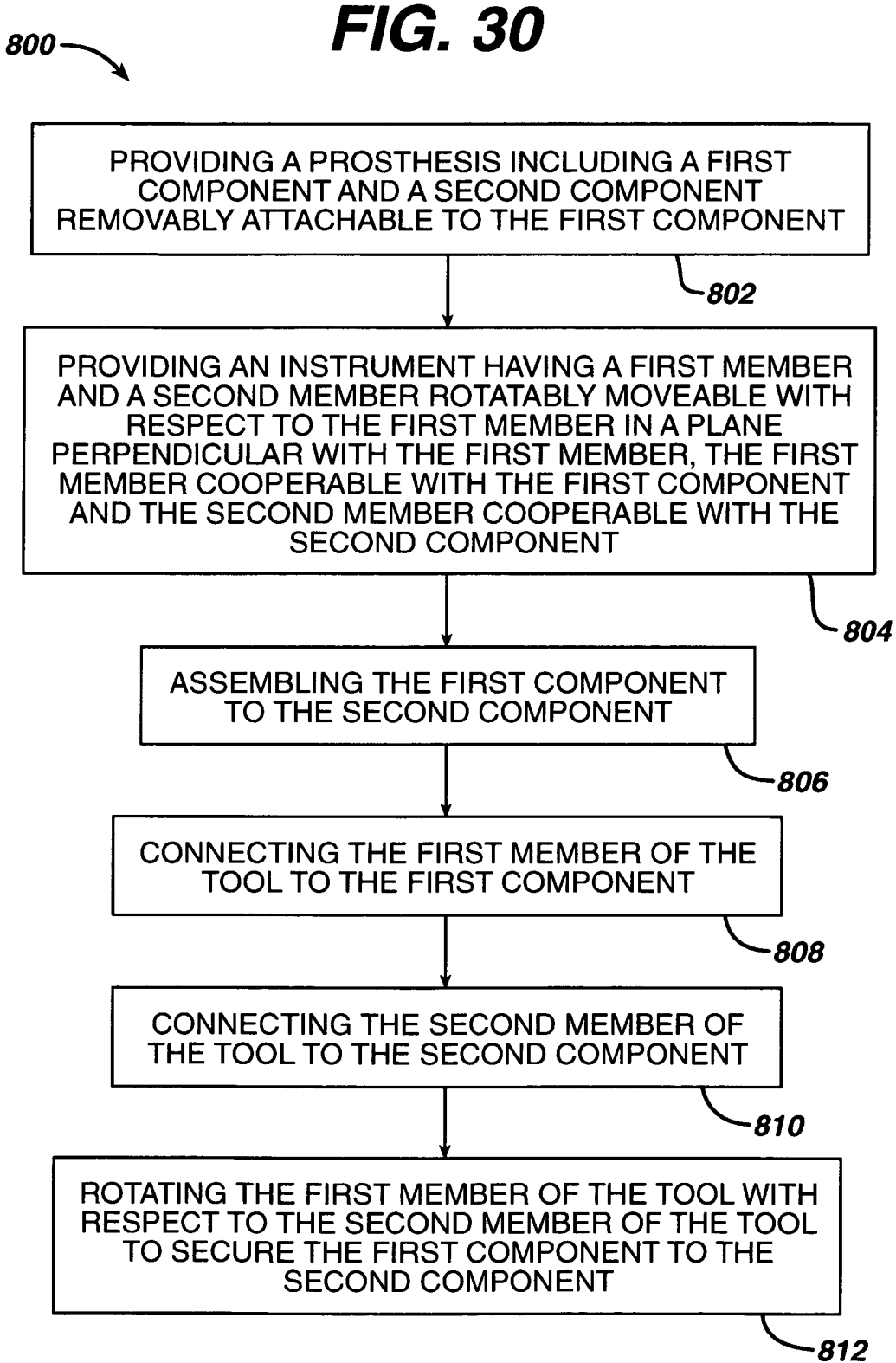

ASSEMBLY TOOL FOR MODULAR IMPLANTS AND ASSOCIATED METHOD

CROSS-REFERENCE TO RELATED APPLICATIONS

This application is a Continuation of U.S. patent application Ser. No. 10/606,401, filed Jun. 25, 2003 (now U.S. Pat. No. 7,297,166 issued Nov. 20, 2007). Cross reference is also made to U.S. application Ser. No. 10/606,303, filed Jun. 25, 2003 and entitled "MODULAR TAPERED REAMER FOR BONE PREPARATION AND ASSOCIATED METHOD", (now U.S. Pat. No. 7,074,224 issued Jul. 11, 2006) and to U.S. application Ser. No. 10/606,304, filed Jun. 25, 2003 and entitled "NON-LINEAR REAMER FOR BONE PREPARATION AND ASSOCIATED METHOD" (now abandoned), the disclosures of which are hereby totally incorporated by reference in their entirety.

TECHNICAL FIELD OF THE INVENTION

The present invention relates generally to the field of orthopaedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

There are known to exist many designs and methods for manufacturing implantable articles, such as bone prostheses. Such bone prostheses include components of artificial joints such as elbows, hips, knees and shoulders.

During performance of a joint replacement procedure, it is generally necessary to provide the surgeon with a certain degree of flexibility in the selection of a prosthesis. In particular, the anatomy of the bone into which the prosthesis is to be implanted may vary somewhat from patient to patient. Such variations may be due to, for example, the patient's age, size and gender. For example, in the case of a femoral prosthesis, the patient's femur may be relatively long or relatively short thereby requiring use of a femoral prosthesis which includes a stem that is relatively long or short, respectively. Moreover, in certain cases, such as when use of a relatively long stem length is required, the stem must also be bowed in order to conform to the anatomy of the patient's femoral canal.

Such a need for prostheses of varying shapes and sizes thus creates a number of problems in regard to the use of a one-piece prosthesis. For example, a hospital or surgery center must maintain a relatively large inventory of prostheses in order to have the requisite mix of prostheses needed for certain situations, such as trauma situations and revision surgery. Moreover, since the bow of the stem must conform to the bow of the intramedullary canal of the patient's femur rotational positioning of the upper portion of the prosthesis is limited thereby rendering precise location of the upper portion and hence the head of the prosthesis very difficult. In addition, since corresponding bones of the left and right side of a patient's anatomy (e.g. left and right femur) may bow in opposite directions, it is necessary to provide (left) and (right) variations of the prosthesis in order to provide anteversion of the bone stem, thereby further increasing the inventory of prostheses which must be maintained.

As a result of these and other drawbacks, a number of modular prostheses have been designed. As its name implies, a modular prosthesis is constructed in modular form so that the individual elements or figures of the prosthesis can be selected to fit the needs of a given patient's anatomy. For example, modular prostheses have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position which conforms to the patient's anatomy while also allowing for a limited degree of independent positioning of the proximal neck component relative to the patient's pelvis.

One issue that arises as a result of the use of a modular prosthesis is the locking of the components relative to one another. In particular, firm reproducible locking of the proximal neck component to the distal stem component is critical to prevent separation of the two components subsequent to implantation thereof into the patient. The need for the firm locking is particularly necessary if the design does not provide for positive locking with weight bearing. As such, a number of locking mechanisms have heretofore been designed to lock the components of a modular prosthesis to one another. For example, a number of modular prostheses have heretofore been designed to include a distal stem component which has an upwardly extending post which is received into a bore defined distal neck component. A relatively long fastener such as a screw or bolt is utilized to secure the post with the bore. Other methods of securing modular components include the impacting of one component onto the other. This method has highly variable results.

Current designs of modular stems include designs in which the modular connection utilizes a tapered fit between the two components. For example, the proximal body may include an internal taper which mates with an external taper on the distal stem. Such a taper connection may be used in conjunction with additional securing means, for example, a threaded connection or may be used alone. It is important that the tapered connection be secure. For example, the proper amount of force must be applied to the tapered connection to properly secure the tapered connection so that the connection can withstand the forces associated with the operation of the stem.

Current attempts to provide a device to adjoin components of a modular joint prosthesis are fraught with several problems. For example, the device may not provide sufficient mechanical advantage to securely lock the components. Further, the ergonomics available to lock the components may not be optimal. Further, a device relying solely on the displacement for a taper connection may not provide sufficient force as there may not be an accurate correspondence of displacement to the clamping force. Further, utilizing a displacement method may make it possible to overtighten and damage the components. Further, prior art solutions may be difficult to manufacture or expensive to make. Further prior art devices may be unsuitable for disconnecting the components. There is thus a need to provide for a assembly and disassembly tool capable of alleviating at least some of the aforementioned problems.

U.S. patent application Ser. No. 10/327,187 entitled "ADJUSTABLE BIOMECHANICAL TEMPLATING & RESECTION INSTRUMENT AND ASSOCIATED METHOD", U.S. patent application Ser. No. 10/327,196 entitled "ALIGNMENT DEVICE FOR MODULAR IMPLANTS AND METHOD" and U.S. patent application Ser. No. 10/327,527 entitled "INSTRUMENT AND ASSOCIATED METHOD OF TRIALING FOR MODULAR HIP STEMS" are hereby incorporated in their entireties by reference.

SUMMARY OF THE INVENTION

According to the present invention, a device is provided for two components of a modular joint prosthesis. The device is particularly well-suited for assembling the proximal stem component to the distal stem component of a modular prosthetic joint stem, such as one for a hip prosthesis. The instrument has a portion that engages, for example, the proximal component and another component that engages the distal component. The instrument applies force on the proximal component and an opposing force on the distal component. For example, the instrument may threadably engage the proximal aspect of the distal stem and apply an opposing force on the proximal shoulder of the proximal body.

The first component of the instrument is caused to rotate with respect to the second component of the instrument. A handle is rotated about the central axis that conveys rotary motion into axial displacement. The axial displacement serves to thereby lock and unlock the taper joining the distal component to the proximal component. The instrument may be designed to yield a specific axial displacement, which is previously determined based upon the specific taper geometry of the implant.

In an embodiment of the present invention, a coupling device threadably engages with the proximal aspect of the distal stem. A counterface contacts the proximal aspect or shoulder of the proximal body in order to provide opposing forces which axially displace the two components relative to each other, thus locking and unlocking the tapered connection. The instrument may be actuated by rotating one handle with respect to the body or another handle. The handle may, for example, travel in a slot, angled relative to the axis of the cylinder, thereby providing axial motion. In other embodiments of the present invention, a standard thread and bolt connection between the first component and the second component provide for the axial motion.

According to one embodiment of the present invention, there is provided an assembly tool for assembly of a first component of a prosthesis to a second component of the prosthesis for use in joint arthroplasty. The tool includes a first member operably associated with the first component. The first member defines a first member longitudinal axis of the first member. The tool also includes a second member operably associated with the second component. The second member defines a second member longitudinal axis of the second member. The second member is adapted to provide relative motion of the second member with respect to the first member when the second member is rotated relative to the first member about the second member longitudinal axis.

According to another embodiment of the present invention there is provided an assembly tool for assembly of a first component of a prosthesis to a second component of the prosthesis for use in joint arthroplasty. The tool includes a first member operably associated with the first component. The first member defines a first member longitudinal axis of the first member. The first member includes a first member relative motion feature and a body defining a generally cylindrical longitudinal opening in the body. The tool also includes a second member operably associated with the second component. The second member has a portion of the second member matingly fitted to the cylindrical longitudinal opening of the first member. The second member defines a second member longitudinal axis of the second member. The second member is adapted to provide relative motion of the second member with respect to the first member along the longitudinal axis of the second member when the second member is rotated relative to the first member about the second member longitudinal axis. The second member includes a second member relative motion feature. The first member relative motion feature and the second member relative motion feature cooperate with each other to provide the relative motion of the first member with respect to the second member. The relative motion of the second member with respect to the first member corresponds to the relative motion of the first component with respect to the second component to urge the second component into engagement with the first component.

According to another embodiment of the present invention there is provided a kit for use in joint arthroplasty. The kit includes an implant for implantation at least partially in the medullary canal of a long bone. The implant has a first component and a second component removably attachable to the first component. The kit also includes an assembly tool including a first member operably associated with the first component. The first member defines a first member longitudinal axis of the first member and a second member operably associated with the second component. The second member defines a second member longitudinal axis of the second member. The second member is adapted to provide relative motion of the second member with respect to the first member when the second member is rotated relative to the first member about the second member longitudinal axis.

According to a further embodiment of the present invention, there is provided a method for providing joint arthroplasty. The method includes the steps of providing a prosthesis including a first component and a second component removably attachable to the first component, providing a instrument having a first member and a second member rotatably moveable with respect to the first member in a plane perpendicular with the first member, the first member cooperable with the first component and the second member cooperable with the second component, assembling the first component to the second component, connecting the first member of the tool to the first component, connecting the second member of the tool to the second component, and rotating the first member of the tool with respect to the second member of the tool to secure the first component to the second component.

The technical advantages of the present invention include the ability of the device to provide sufficient mechanical advantage to properly secure the components to form a secured joint. For example, according to one aspect of the present invention, the first component is joined to the second component by a threaded connection. By changing the pitch of the threadable connection, the mechanical advantage can be increased to provide for a sufficient mechanical advantage.

For example, according to yet another aspect of the present invention, the first component and the second component have outwardly extending handles. The handles may have any suitable length and may be made longer to provide for additional mechanical advantage. Thus the present invention provides for sufficient mechanical advantage to properly secure the prosthesis.

Another technical advantage of the present invention is the ability of the device to provide for optimum ergonomics. For example, according to one aspect of the present invention, the device is held and actuated by opposed extending handles which may be easily gripped by the surgeon and rotated relative to each other to secure the joint. Thus, the present invention provides for simple optimum ergonomics.

Yet another technical advantage of the present invention includes the ability of the device to provide for a measurement of forces in addition to the measurement of displacement. Due to frictional forces and additional complications, displacements of the device do not always directly linearly correspond to the forces that may be applied by the device. Therefore, there is an advantage to be able to measure the force applied by the device in addition to the displacement of the device. For example, according to another aspect of the present invention, a handle of the device may include a torque measuring feature which may be used to measure the torque applied to the device. Alternatively or in addition thereto, the device may include a force washer or other force transducers along the axial body of the instrument in order that the forces applied may be directly measured.

Another technical advantage of the present invention includes the ability of the device to limit the displacement of the instrument and therefore to limit the force applied to the prosthesis. If excessive force is applied to the prosthesis it is possible to overtighten and damage the component. For example, according to one aspect of the present invention, the displacement is physically limited by a helical opening of limited length or by a limited amount of threaded engagement between the two components. It is also possible to provide for a device with a break-away torque limiter that limits the amount of torque that the device may apply. Thus, the present invention provides for an ability to avoid overtightening of the prosthesis components.

Another technical advantage of the present invention is its simple and inexpensive design. For example, according to one aspect of the present invention, the device includes a cylindrical tube and a rod which slidably fits within the cylindrical tube. The tube and rod are threadably connected so that when one component is rotated with respect to the other one, the one component moves axially relative to the other one providing for a simple, inexpensive way of utilizing a device to disassemble or assemble a component.

An additional advantage of the present invention includes the ability of the device to be utilized simply and easily to disconnect as well as to connect the components of a modular prosthesis. For example, according to one aspect of the present invention, a component may be placed onto the assembly device to provide for connecting features to disassemble the device. Thus, the present invention provides for a simple and quick way of being utilized to disassemble as well as to assemble a prosthesis.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 5 is an exploded plan view of the modular hip stem of FIG. 4;

FIG. 6 is a partial plan view of a proximal body of another embodiment of a two pieced modular hip stem than may be assembled with the assembly tool of FIG. 2 without the counter bore for the assembly nut as in the hip stem of FIG. 5;

FIG. 30 is a flow chart of a method of using the assembly tool of the present invention according to another embodiment of the present invention.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
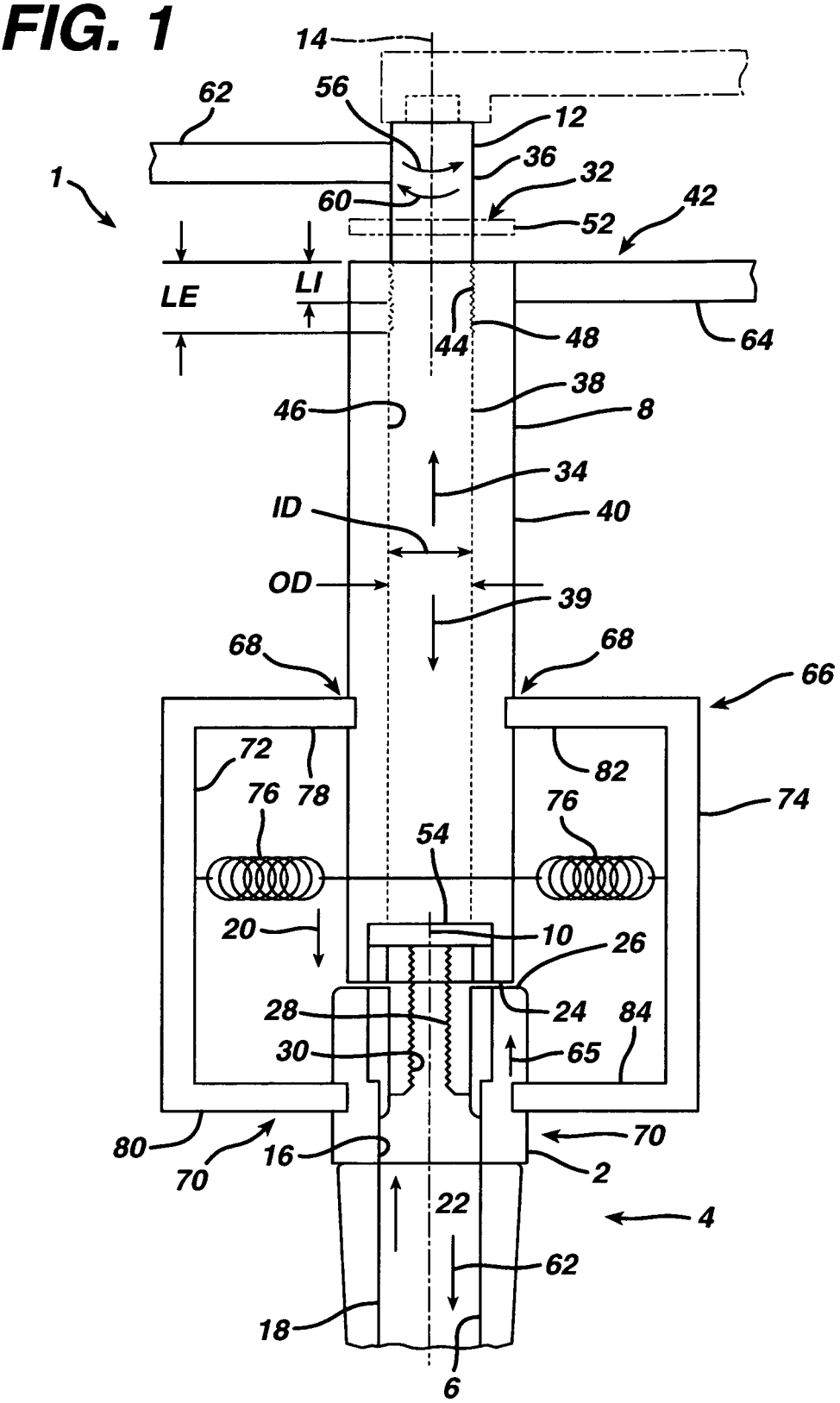
FIG. 1 is a plan view partially in cross-section of an embodiment of the present invention in the form of an assembly tool including a threaded connection in operation with a prosthesis.

According to the present invention and referring now to FIG. 1, assembly tool 1 according to the present invention is shown. The assembly tool 1 is used for assembly of a first component 2 of a prosthesis 4 to a second component 6 of the prosthesis 4 for use in joint arthroplasty. The tool 1 includes a first member 8 operably associated with the second component 6. The first member 8 defines a first member longitudinal axis 10 of the first member 8. The tool 1 also includes a second member 12 operably associated with the second component 6. The second member 12 defines a second member longitudinal axis 14 of the second member 12. The second member 12 is adapted to provide relative motion of the second member 12 with respect to the first member 8 when the second member 12 is rotated relative to the first member 8 about the second member longitudinal axis 14.

The assembly tool 1 is suited for use with the prosthesis 4 when, for example, the prosthesis 4 includes the first component 2 and the second component 6 which are engaged and disengaged by relative motions along an axis. For example, the assembly tool 1 is suitable when the prosthesis 4 includes components which are connected by a tapered connection. For example, as shown in FIG. 1, the first component 2 includes an internal taper 16 that mates with an external taper 18 located on the second component 6.

As shown in FIG. 1, the first component 2 is engaged with the second component 6 when the first component 2 moves in the direction of arrow 20 and/or when the second component 6 moves in the direction of arrow 22. As shown in FIG. 1, the first member 8 is operably associated with the first component 2 while the second member 12 is operably associated with the second component 6. To provide for the operable association of the components, it should be appreciated that the first member 8 includes a first member operating feature 24 which is operably associated with a first component operating feature 26 of the first component 2. Similarly, the second member includes a second member operating feature 28 which cooperates with a second component operating feature 30 of the second component 6.

For simplicity, since the first member 8 and the first component 2 are merely required to prevent motion of the two components toward each other, the first member 8 and the first component 2 may be designed such that the first member operating feature 24 may be in the form of a bottom and/or surface. Similarly, the first component operating feature 26 may be in the form of a top surface of the first component 2.

The second member operating feature 28 and the second component operating feature 30 may be any features capable of urging the second component 6 upwardly in the direction of arrow 22. For example, for simplicity, the second member operating feature 28 may be in the form of internal threads formed on the second component operating feature 26, which may mate with external threads 30 formed on the second component 6.

The first member 8 and the second member 12 may have any shape or configuration capable of providing relative motion along first member longitudinal axis 10 and second member longitudinal axis 14. For example, and as shown in FIG. 1, the first member 8 may be in the form of a hollow component or tube. Similarly, the second member 12 may be in the form of a rod or cylinder which may slidably fit within the first member 8. As shown in FIG. 1, the first member 8 may include a longitudinal opening 32.

In order to move the second component 6 into engagement with the first component 2, it should be appreciated that the second member 12 must move in the direction of arrow 34 with respect to the first member 8. In order to provide relative motion between the second member 12 and the first member 8, as shown in FIG. 1, the second member 12 may include a rod portion 36 having a cylindrical periphery 38 thereof. The first member 8 may, as shown in FIG. 1, include a cylindrical tubular portion 40 that defines the opening 32 therein. The rod periphery 38 of the second member 12 defines an outside diameter OD which is matingly fitted with dimension ID of the opening 32 of the tubular portion 40.

As shown in FIG. 1, the relative motion of the first member 8 with respect to the second member 12 may be controlled by, for example, a relative motion feature 42. As shown in FIG. 1, the relative motion feature 42 may be in the form of a threaded connection. The threaded connection 42 may, for example, as shown in FIG. 1, include a first member relative motion feature 44 in the form, of for, example internal threads. The internal threads 44 are formed on internal periphery 46 of the tubular portion 40 of the first member 8.

The relative motion feature 42 may also include a second member relative motion feature 48. Second member relative motion feature 48 may be in the form of, for example, external threads formed on rod portion 36 of the second member 12. The threads 44 and 48 cooperate to provide the relative motion of the second member 12 in the direction of arrow 34 with respect to the first member 8. The threads 44 and 48 are matingly engaged and have a pitch selected to provide for the desired mechanical advantage.

Preferably and as shown in FIG. 1, the amount of relative motion of the first member 8 with respect to the second member 12 is limited. Such a limited relative motion of the first member 8 with respect to the second member 12 correspondingly limits the motion of the first component with respect to the second component 6 thus preventing overtightening of the prosthesis 4. The motion of the first member 8 with respect to the second member 12 may be accomplished in any suitable fashion. For example, the external threads 48 may have a thread length LE which is slightly greater than the thread length LI of the internal threads 44 of the first member 8. Thus, the motion in the direction of arrows 34 and 38 of the component 12 with respect to component 8 is limited by the difference of the thread lengths LE and i. It should be appreciated that the threads 44 and 46 may only limit the motion of the members 8 and 12 if the major diameters of the threads 44 and 48 provide interference with the first member 8 or the second member 12. It should be appreciated that stops (not shown) may be utilized to limit the relative motion of the first member 8 with respect to the second member 12. A cap 52 and a collar 54, both secured to first meter 8 and both shown in phantom, may be utilized to limit the relative motion of the first member 8 with respect to the second member 12.

It should be appreciated that in order to move the second member 12 in the direction of arrow 34 with respect to the first member 8, the second member 12 must be rotated in the direction of arrow 56 with respect to first member 8. This motion assembles the components 2 and 6. Similarly, it should be appreciated that in order for the second member 12 to move in the direction of arrow 39 with respect to the first member 8, the second member 12 must be rotated in the direction of arrow 60 with respect to the first member 8. This motion disassembles the components 2 and 6.

To provide the sufficient torque or mechanical advantage for rotating the second member 12 in the direction of arrow 56 and 60, it should be appreciated that the second member 12 may include a second member handle 62 extending outwardly from the rod portion 36 of the second member 12. Similarly, it should be appreciated that to resist the force applied by the second member handle 62, the first member 8 may similarly include a first member handle 64 extending outwardly from the tubular portion 40 of the first member 8. The handles 62 and 64 may have any suitable size and shape capable of receiving for example the hands of the surgeon or operator of the assembly tool 1.

It should be appreciated that the assembly tool 1 may likewise be utilized to disassemble the first component 2 from the second component 6. It should be appreciated that the assembly tool 1 may be adapted for use for the disassembly of the first component 2 from the second component 6. It should be appreciated that one of the first member 8 and the second member 12 may be associated with one of the first component 2 and the second component 6 such that as the first member 8 is moved relative to the second member 12, the first component 2 may be disassembled from the second component 6. To accomplish this, one of the first member 8 and the second member 12 is operably associated with the first component 2 while the other of the first member 8 and the second member 12 is operably associated with the second component 6.

For example, and as shown in FIG. 1, the second member 12 may be operably associated with the second component 6 by, for example, utilizing the second member cooperating feature 28 in the form of internal threads to cooperate with the second component operating feature 30 in the form of external threads. The first member 8 is similarly operably associated with the first component 2.

In order that the second component 6 may be forced to move in the direction of arrow 63 while the first component 2 is required to move in the direction of arrow 65, the first component 2 must be restrained by the first member 8. The first component 2 is held against the first member 8 by, for example, a third member 66.

The third member 66 cooperates with the first member 8 and the first component 2 to hold the two components against each other. The third member 66 may cooperate with the first member 8 and the first component 2 in any suitable fashion. For example, the first member 8 may include a first member disassembly operating feature 68 which cooperates with the third member 66. Similarly, the first component 2 may include a first component disassembly operating feature 70 which cooperates with the third member 66.

The third member 66 may have any suitable design or shape and may, for example, be in the form of first fork 72 and second fork 74. The forks 72 and 74 may be urged together by, for example, springs 76. The first fork 72 may include a first tine 78 which engages with the first member disassembly operating feature 68 in the form of, for example, a first member groove. Similarly, the first fork 72 may include a second tine 80 for cooperation with the first component operating disassembly feature 70 in the form of, for example, a second component groove. The second fork 74 may include a first tine 82 for cooperation with the first member groove 68 as well as a second tine 84 for engagement with the second groove 70.

When utilizing the assembly tool 1 to assemble the first component 2 to the second component 6 the third member 66 is not used. The assembly tool 1 is positioned with respect to the prosthesis 4 such that the internal threads 28 of the second member 12 engage the external threads 30 of the second component 6. The internal threads 28 and the external threads 30 are threaded into engagement with each other and the second member 12 is rotated with respect to the second component 6 until the bottom end surface 24 of the first member 8 is in contact with the top surface 26 of the first component 2. At this point, the second member handle 62 is rotated in the direction of arrow 56 until the second member handle has come to the stop created by the relative motion feature 42.

When utilizing the assembly tool 1 to disassemble the first component 2 from the second component 6 the third member 66 is utilized and placed in position on the assembly tool 1. The forks 72 and 74 of the third member 66 are placed in position in the first member grooves 68 and the first component grooves 70. The top surface 26 of the first component 2 is thus in contact with the bottom end surface 24 of the first member 8. The second component 6 is then threadably engaged into the second member 12. The second member handle 62 is then rotated in the direction of arrow 60 until the relative motion feature 42 ends the movement of the second member handle 62 thereby disassembling the first component 2 from the second component 6.

Figure 2:
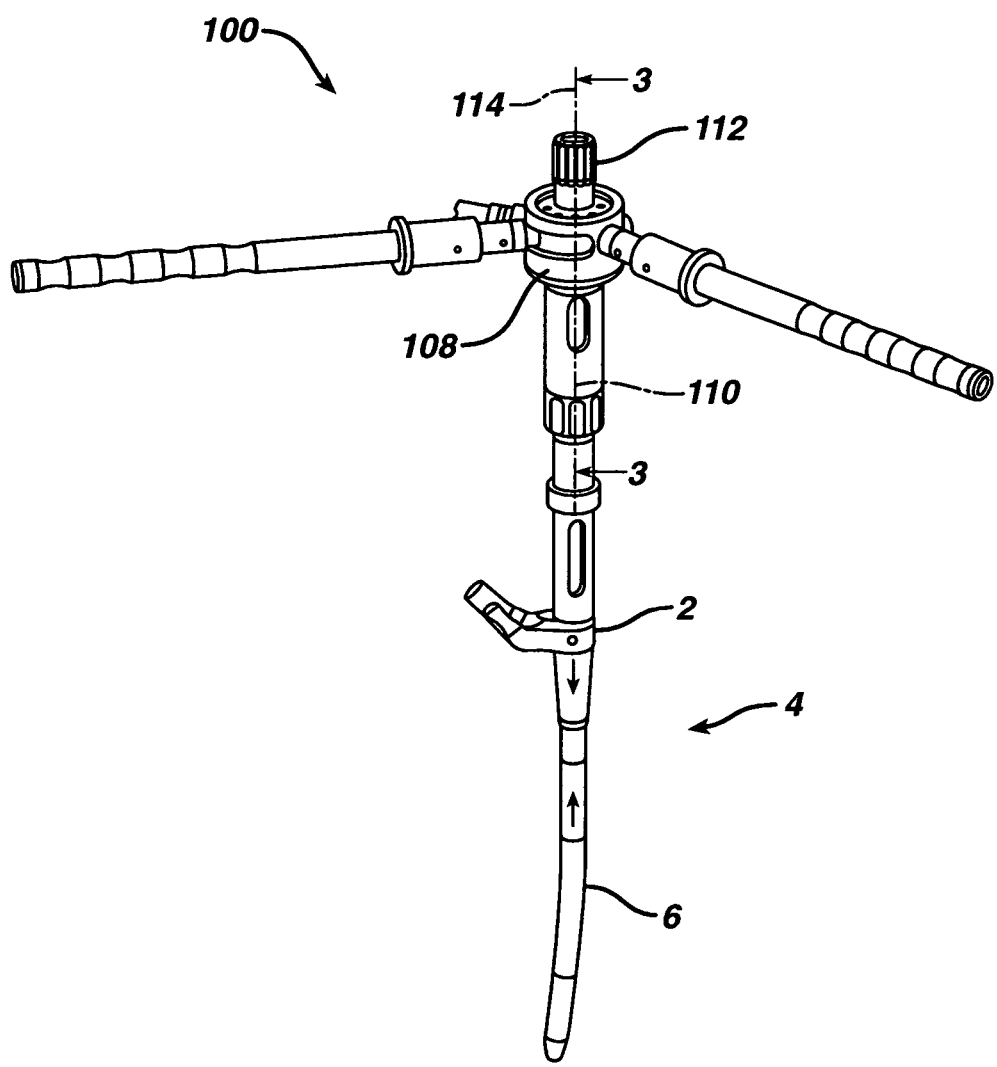
FIG. 2 is a perspective view of another embodiment of the present invention in the form of an assembly tool with a spiral cam and follower mechanism shown in engagement with a prosthesis.

Referring now to FIG. 2, another embodiment of the present invention is shown as assembly tool 100. The assembly tool 100 is utilized for assembling the first component 2 of the prosthesis 4 to the second component 6 of the prosthesis 4. The prosthesis 4 may be used, for example, in joint arthroplasty. The tool 100 is similar to the tool 1 of FIG. 1 and includes a first member 108 operably associated with the first component 2. The first member 108 defines a first member longitudinal axis 110 thereof. The assembly tool 100 further includes a second member 112 which is operably associated with the second component 6. The second member 112 defines a second member longitudinal axis 114 thereof. The second member 112 is similar to second member 2 of the assembly tool 1 of FIG. 1. The second member 112 is adapted to provide relative motion of the second member 112 with respect to the first member 108 when the second member 112 is rotated relative to the first member 108 about the second member longitudinal axis 114.

The assembly tool 100 may be configured such that the relative motion of the second member 112 with respect to the first member 108 corresponds to the relative motion of the first component 2 with respect to the second component 6 to urge the second component 6 into engagement with the first component 2.

Figure 3:
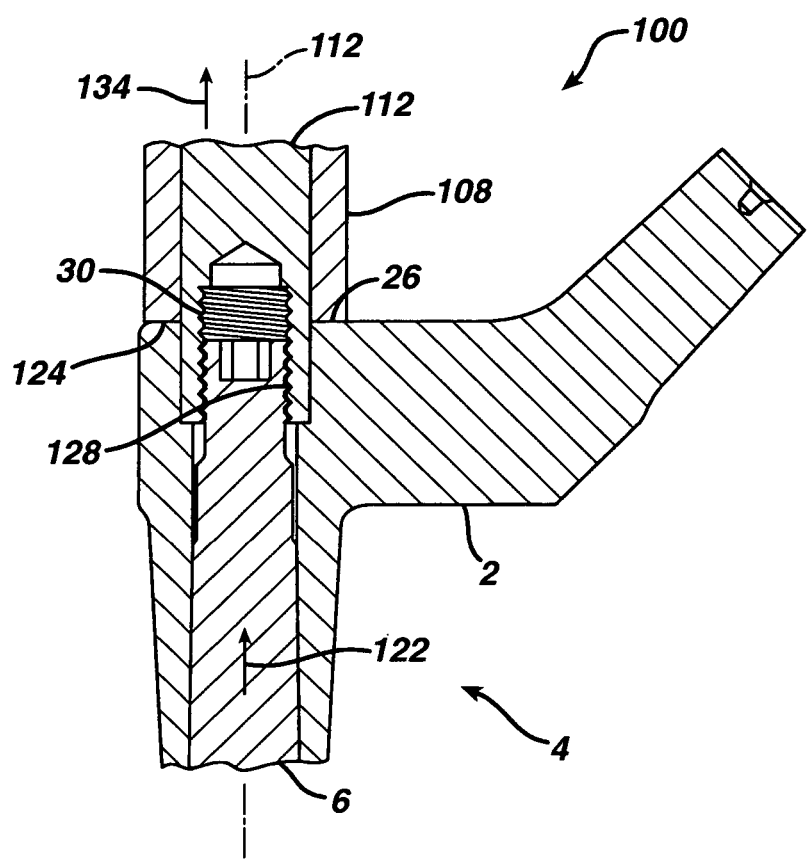
FIG. 3 is a cross section view of FIG. 2 along the line 3-3 in the direction of the arrows.

Referring now to FIG. 3, the engagement of the assembly tool 100 with the prosthesis 4 is shown in greater detail. As shown in FIG. 3, the second component 6 includes a second component operating feature in the form of external threads 30. The external threads 30 are matingly fitted to, for example, internal threads 128 formed on second member 112. The first component 2 includes a operating feature in the form of, for example, a top surface 26 which mates with bottom surface 124 of the first member 108 of the tool 100.

Since the first member 108 is in contact with the first component 2 as the first component moves in the direction of arrow 122 relative to the first component 2, the second member 112, which threadably secured to the second component 6 moves in the direction of arrow 134 relative to the first member 108. Thus, the relative motion of the second member 112 with respect to the first member 108 in the direction of arrow 134 corresponds to the relative motion of the second component 6 with respect to the first component 2 in the direction of arrow 122.

Figure 4:
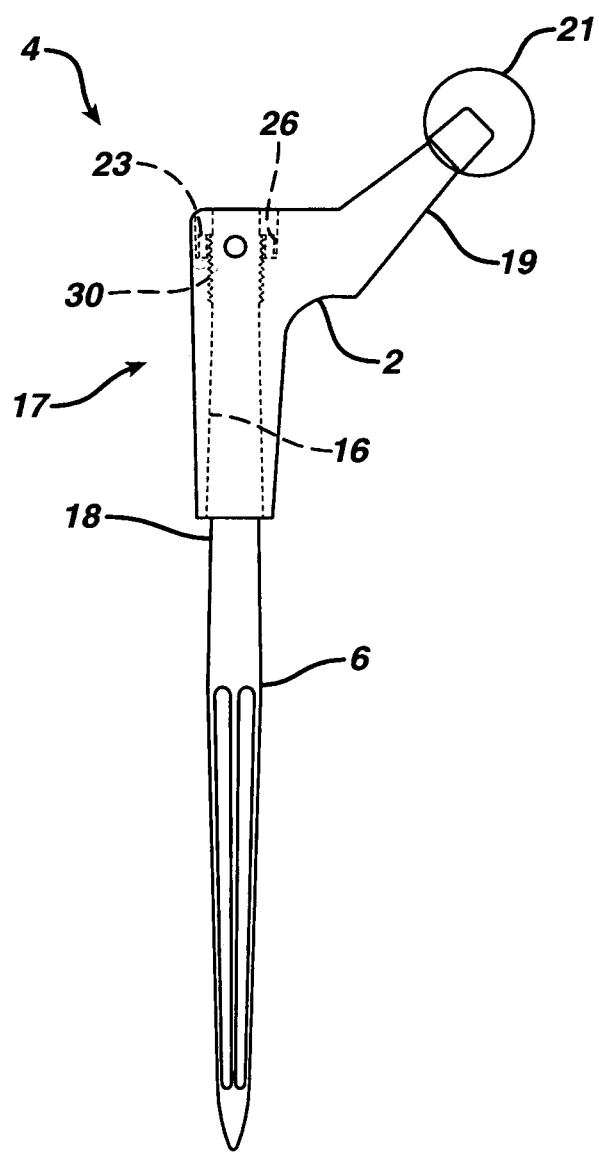
FIG. 4 is a plan view of a two pieced modular hip stem than may be assembled with the assembly tool of FIG. 2.

Referring now to FIG. 4, the prosthesis 4 is shown in greater detail. The prosthesis 4 as shown in FIG. 4 includes a taper connection 17. As shown in FIG. 4, the taper connection consists of the external taper 18 formed on the distal stem 6 that engages with internal taper 16 formed on the first component in the form of the proximal body 2.

It should be appreciated that the prosthesis for use with the assembly tool 1 or 100 of FIGS. 1 and 2, respectively, may include a proximal body 2 and a distal stem 6 which have an interference connection that is, for example, a interference connection of a cylindrical bore to a cylindrical stem, as well as, a splined non-uniform cross-section stem to a splined or non-uniform cross-section opening. It should further be appreciated that proximal body and distal stem of the prosthesis 4 for use with the assembly tool of the present invention may include a taper connection in which the distal stem has an internal taper and the proximal body has an external taper.

Again referring to FIG. 4, the prosthesis 4 as shown may include external threads 30 formed on the distal stem 6. The proximal body 2 may include a neck 19 to which a head 21 may matingly be fitted. As an additional precaution in assuring that the proximal body 2 remains secured to the distal stem 6, the prosthesis 4 may further include a nut 23 which threadably engages the external threads 30 of the distal stem 6.

Referring now to FIG. 5, the prosthesis 4 is shown with the proximal body 2 disassembled from the distal stem 6. The external taper 18 of the distal stem 6 is defined by an included angle β1. In order that the proximal body 2 fits securely to the distal stem 6, the proximal body 2 includes the internal taper 16 defined by included angle β2. The angles β1 and β2 may be generally the same. Alternatively the taper angle may be divergent. The angles β1 and β2 should be chosen, such that the fit of the proximal body 2 to the distal stem 6 is secure.

Referring now to FIG. 6, an alternate prosthesis for use with the assembly device of the present invention is shown as prosthesis 204. Prosthesis 204 includes a proximal body 202 which does not include a counterbore. Prosthesis 204 may include a nut 223 which mates with outer face 226 that is not recessed. The nut 223 threadably engages distal stem 206.

Figure 7:
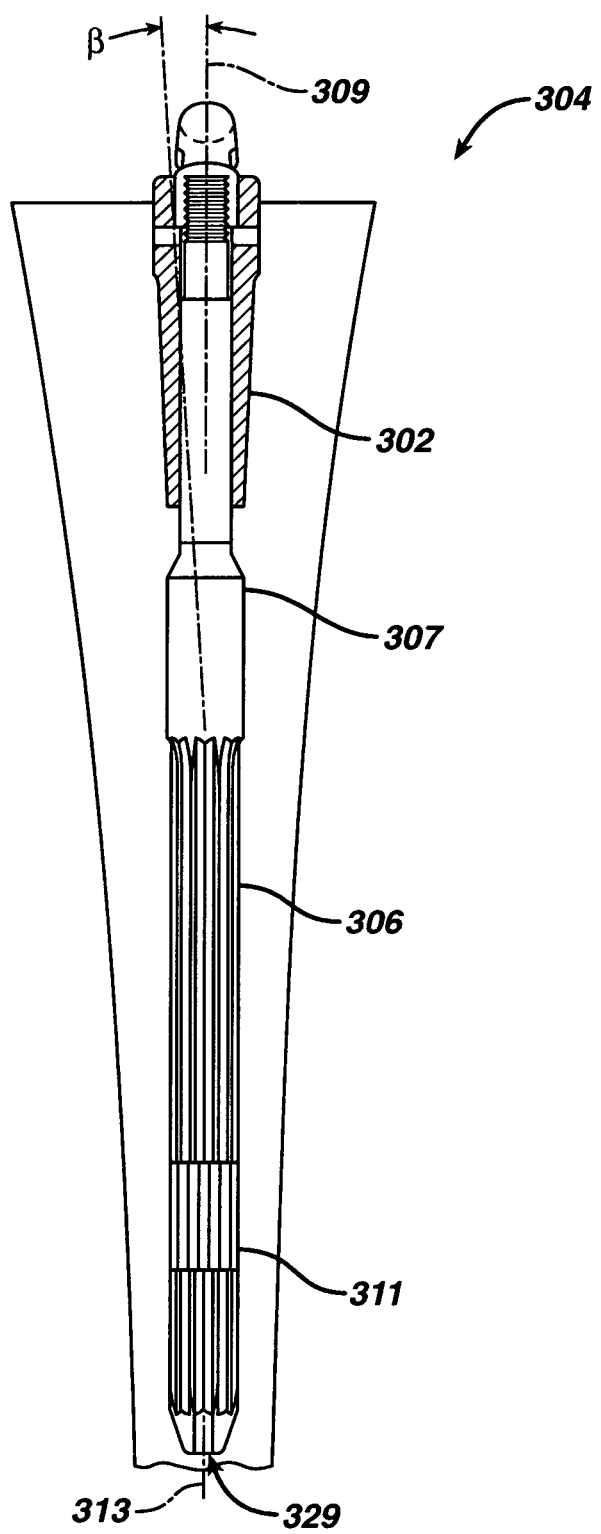
FIG. 7 is a lateral view partially in cross section of the modular hip stem of FIG. 4.

Referring now to FIG. 7, an alternate embodiment of a prosthesis that may be utilized with the assembly tool 1 and 100 of FIGS. 1 and 2, respectively, is shown as prosthesis 304. The prosthesis 304 includes a proximal body 302 similar to the proximal body 2 of the prosthesis 4 of FIG. 4. The prosthesis 304 also includes a distal stem 306 that is different than the distal stem 6 of the prosthesis 4 of FIG. 4. The distal stem 306 is bent and has a proximal portion 307 having a longitudinal centerline 309 and a distal portion having a longitudinal centerline 313. The centerlines 309 and 313 form angle β therebetween. The distal stem 306 may further include a elongated slot 329 extending axially from the end of the stem 306.

Figure 8:
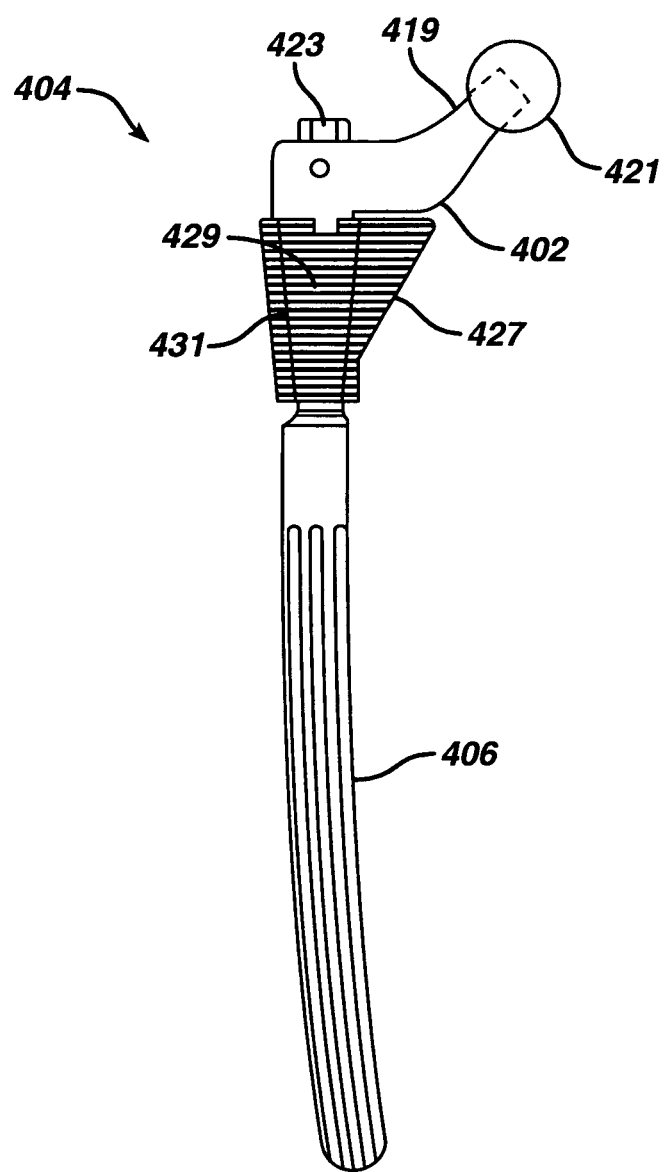
FIG. 8 is a plan view of a three piece modular hip stem with a nut that may be assembled with the assembly tool of FIG. 2.
Figure 9:
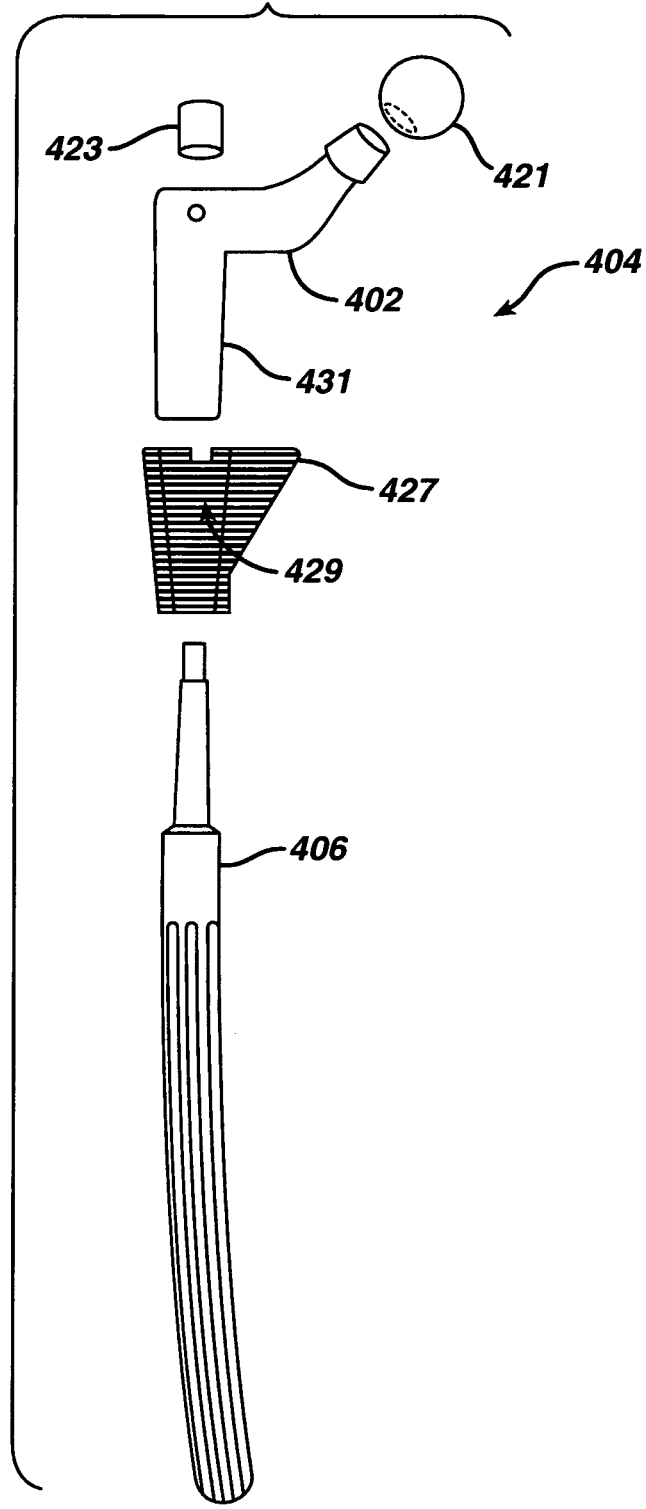
FIG. 9 is an exploded plan view of three piece modular hip stem of FIG. 8.

Referring now to FIGS. 8 and 9, another embodiment of a prosthesis for use with the assembly tool of the present invention is shown as prosthesis 404. Prosthesis 404 is similar to the prosthesis 304 of FIG. 7. Prosthesis 404 includes a proximal body 402 which is connected to a distal stem 406. The proximal body 402 includes a neck 419 to which a head 421 may be positioned. The prosthesis 404 may further include a nut 423 to assist in connecting the proximal body 402 to the distal stem 406. The prosthesis 404 may further include an external sleeve 427 which is fitted to the proximal body 402 by means of an internal taper 429 which mates with an external taper 431 on the proximal body 402. The stem 406 may be bent in a continuous arc.

Figure 10:
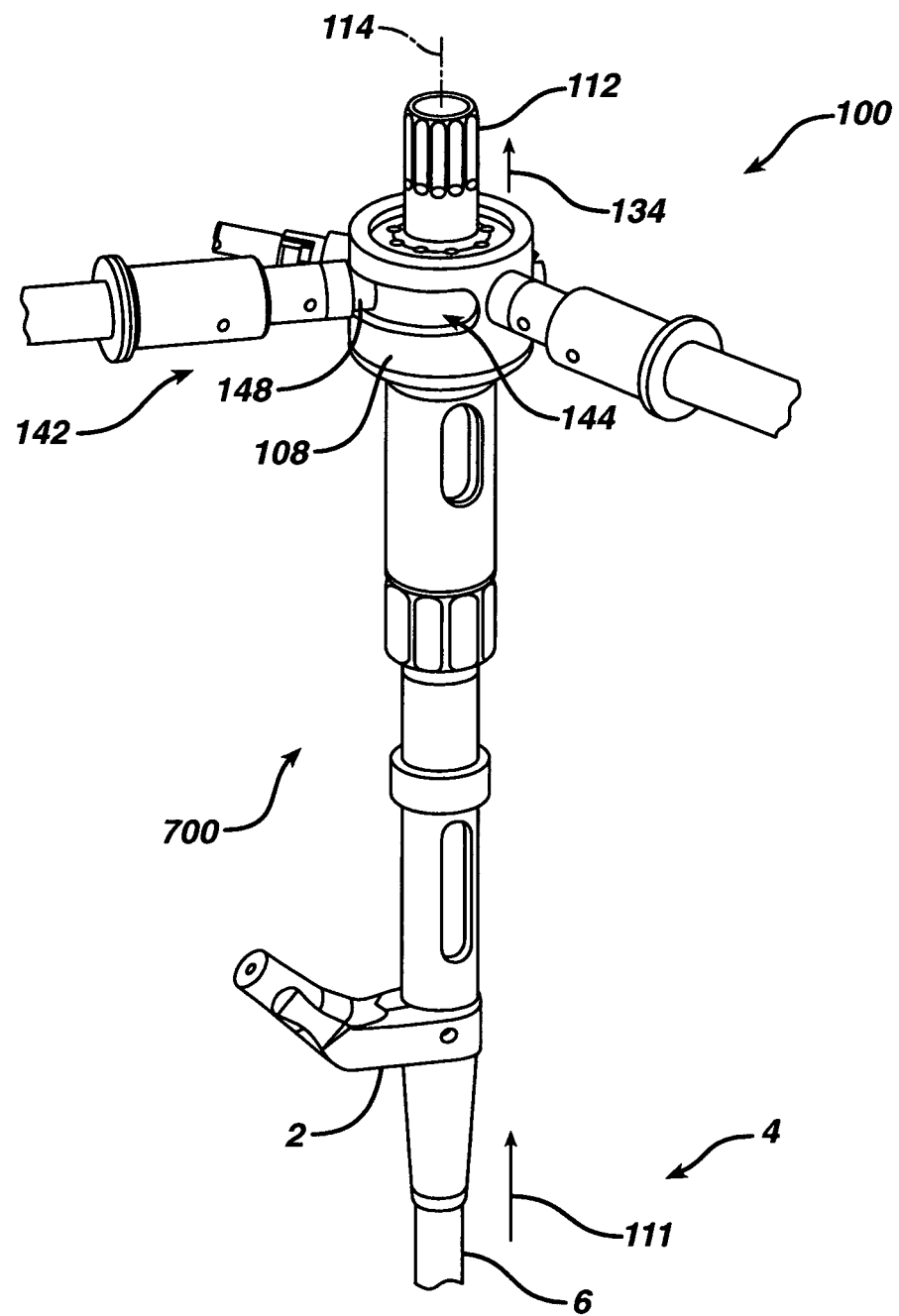
FIG. 10 is a perspective view of the assembly tool of FIG. 2 installed onto the two-piece modular stem of FIG. 4.
Figure 11:
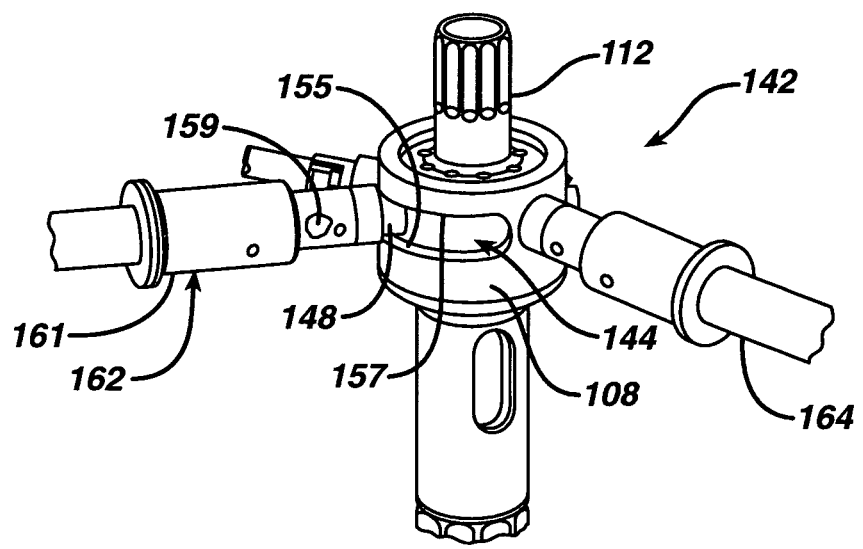
FIG. 11 is a partial perspective view of the assembly tool of FIG. 2 showing the inclined actuating area in greater detail.

Referring now to FIG. 10, the assembly tool 100 is shown in position on the prosthesis 4. The first member 108 is in contact with the first component 2 and the second member 112 is threadably engaged to the second component 6. The assembly tool 100 is utilized to move the second component 6 in the direction of arrow 111 with respect to the first component 2. This relative motion is accomplished by moving the second member 112 in the direction of arrow 134 in relation to the first member 108.

The relative motion of the first member 108 with respect to the second member 112 may be accomplished by, for example, a relative motion feature 142. The relative motion feature 142 may include a first member relative location feature 144 in the form of slot 144 within which a second member relative motion feature 148 in the form of, for example, a pin is rollably restrained with the slot 144. The relative motion feature 142 is utilized to move the second member 112 about the second member longitudinal axis 114 with respect to the first member 108.

Referring now to FIGS. 11, 12, 13, 14 and 15, the relative motion feature 142 is shown in greater detail.

Figure 16:
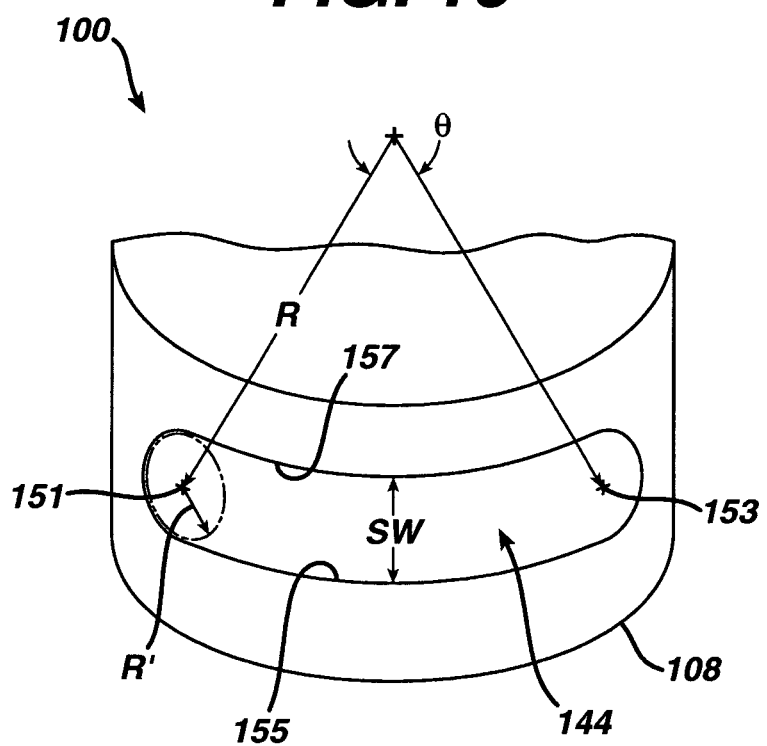
FIG. 16 is a partial perspective view of the assembly tool of FIG. 2 showing spiral cam portion of the ramp actuation mechanism in greater detail.

As shown in FIG. 16, the slot 144 extends from first centerline 151 to second centerline 153. The centerlines 151 and 153 represent the arcuate end portions of the slot 144 defined with a radius R' equal to the slot width SW divided by two. The slot 144 is defined by a first assembly load surface 155 and an opposed second disassembly load surface 157. The load surfaces 155 and 157 are parallel to each other and spaced apart a distance equal to SW or the slot width SW.

A slot length angle θ defines the arcuate difference from first member centerline 110 along slot radius R of the first member 108 between the first centerline 151 and the second centerline 153. The angle θ preferably selected to provide for the proper displacement of the assembly tool 100. The proper displacement of the assembly tool 100 may be predetermined by calculating the desired locking force on the joint of the prosthesis 2.

Figure 12:
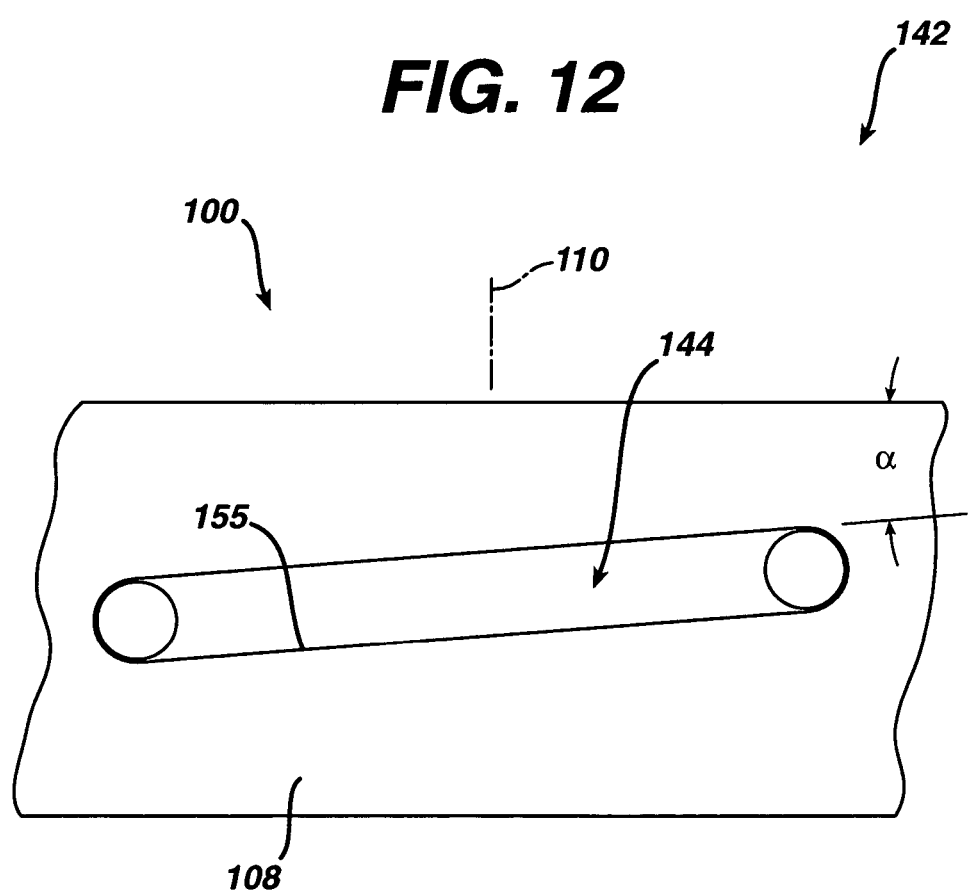
FIG. 12 is a partial unwound view of the inclined actuating area of the assembly tool of FIG. 2 showing the inclined actuating area in greater detail.

Referring to FIG. 12, the assembly load surface 155 is inclined relative to a surface perpendicular to the longitudinal axis 110 of the first member 108 at a ramp angle of α. The angle α, as well as, the radius R (see FIG. 16) affect the displacement of the assembly tool 100.

The dimensions of the relative motion feature 142 may be properly selected by using the formula below:

$$DI = (\theta/360) \times \pi \times 2R \times \tan \alpha$$

Where:
θ=the angular arm displacement in radians
R=the slot 144 radius from centerline 110 in inches
DI=the displacement in inches.
α=the ramp angle in degrees.

Figure 17:
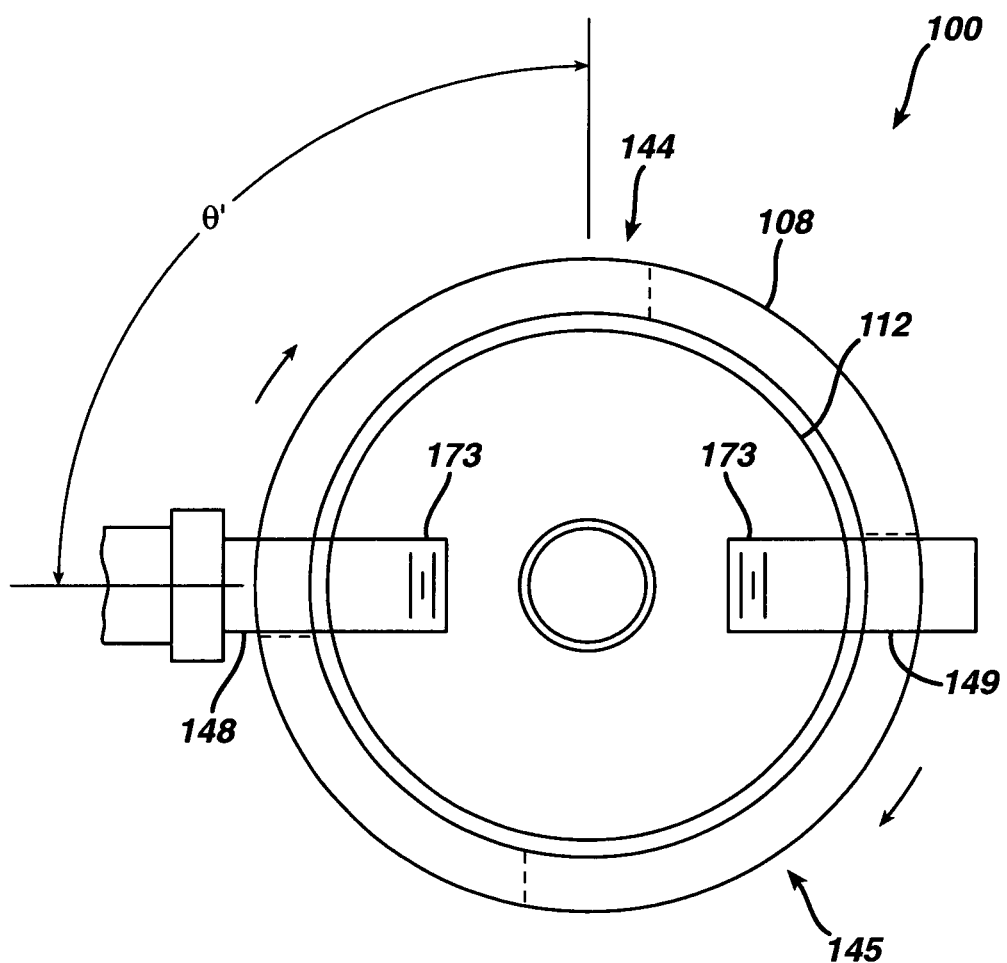
FIG. 17 is a partial top view of the assembly tool of FIG. 2 partially disassembled, showing the spool of the ramp actuation mechanism in greater detail.

Referring now to FIG. 17, the assembly tool 100 may include a second pin 149 opposed to the first pin 148 which matingly fits within a second slot 145 opposed to the first slot 144. First and second pins 148 and 149 are preferably diametrically opposed and the first slot 144 and the second slot 145 are likewise preferably diametrically opposed. The second pin 149 and the second slot 145 serve to balance the forces and loads upon the assembly tool 100.

Referring again to FIG. 11, the assembly tool 100 may include an actuating arm 162 similar to arm 62 of tool 1 of FIG. 1 and a restraining arm 164 similar to arm 64 of tool 1 of FIG. 1. The actuating arm 162 and the restraining arm 164 may be, for example, modular. The arm 162, for example, may include an arm connecting base 159 and an arm extension 161 removably connectable to the arm connecting base 159.

Figure 18:
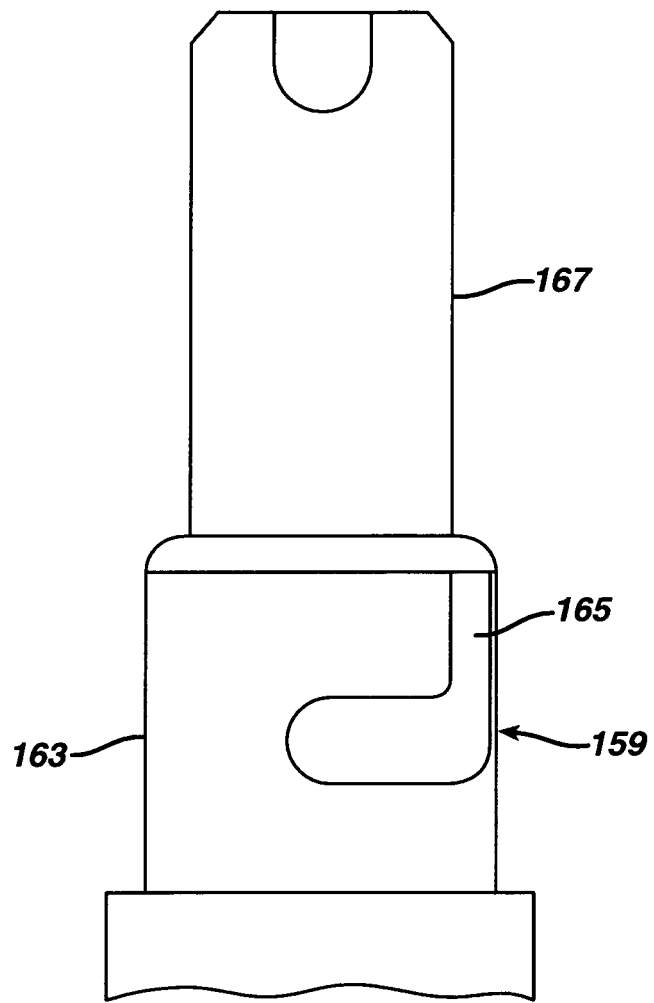
FIG. 18 is a partial enlarged plan view of the assembly tool of FIG. 2 showing the connector for cooperation with the actuation arm in greater detail.

Referring now to FIG. 18, the arm connecting base 159 is shown in greater detail. The arm connecting base 159 includes a base 163 including a bayonet-type groove 165. A stem 167 may extend from the base 163.

Figure 19:
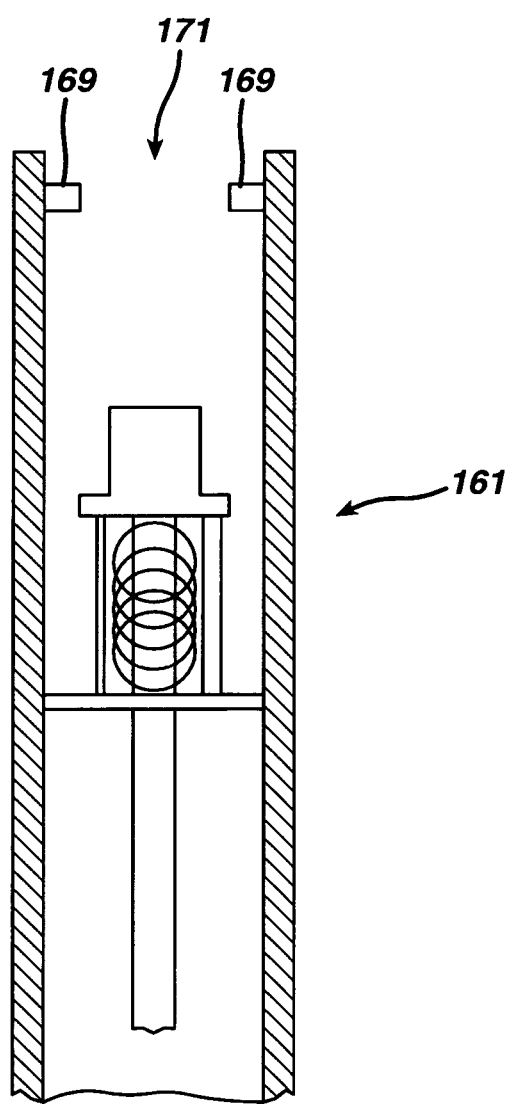
FIG. 19 is a partial enlarged plan view partially in cross section of the assembly tool of FIG. 2 showing the connector of the actuation arm in greater detail.

Referring now to FIG. 19, the arm extension 161 is shown in greater detail. The arm extension 161 may include a pair of pins 169 extending toward the opening 171 in the arm extension 161. The opening 171 receives the base 163 and the stem 167 of the arm connecting base 159 (see FIG. 18).

Referring again to FIG. 17, the construction of the pins 148 and 149 are shown in greater detail. To provide for rolling contact of the pins 148 and 149 against the slots 144 and 145, respectively, the pins 148 and 149 are preferably rotatably mounted on pin stems 173. The pin stems 173 may be threadably connected to the second member 112. It should be appreciated that the pins 148 and 149 may be mounted to the pin stems 173 by means of needle bearings (not shown).

Figure 20:
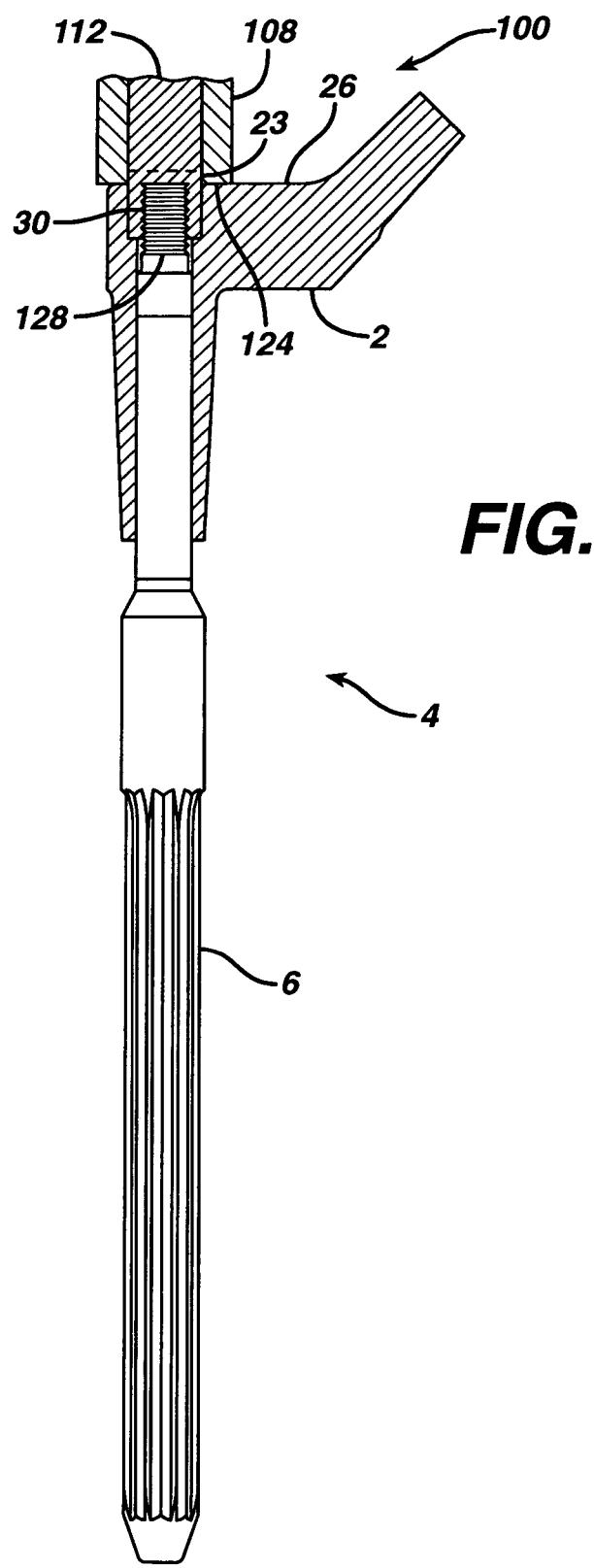
FIG. 20 is a plan view partially in cross section of the implant of FIG. 4 showing the implant in engagement with the assembly tool of FIG. 2.

Referring now to FIG. 20, the prosthesis 4 is shown in engagement with the assembly tool 100. Surface 124 of the first member 108 of the assembly tool 100 is placed against top face 26 of the proximal body 2 of the prosthesis 4. The internal threads 128 of the second member 112 of the assembly tool 100 is threadably engaged with external threads 30 of the stem 6 of the prosthesis 4. After the prosthesis 4 has been assembled utilizing the assembly tool 100, nut 23 shown in phantom is secured to the external threads of the stem 6.

Figure 21:
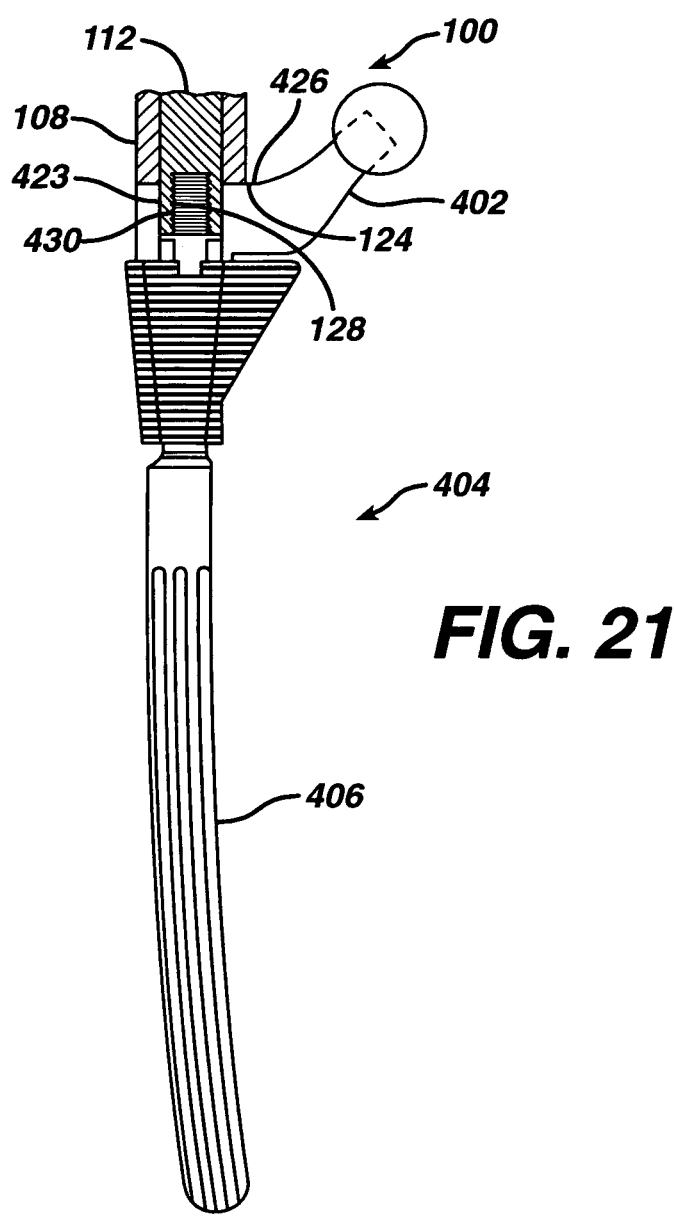
FIG. 21 is a plan view partially in cross section of the implant of FIG. 8 showing the implant in engagement with the assembly tool of FIG. 2.
Figure 22:
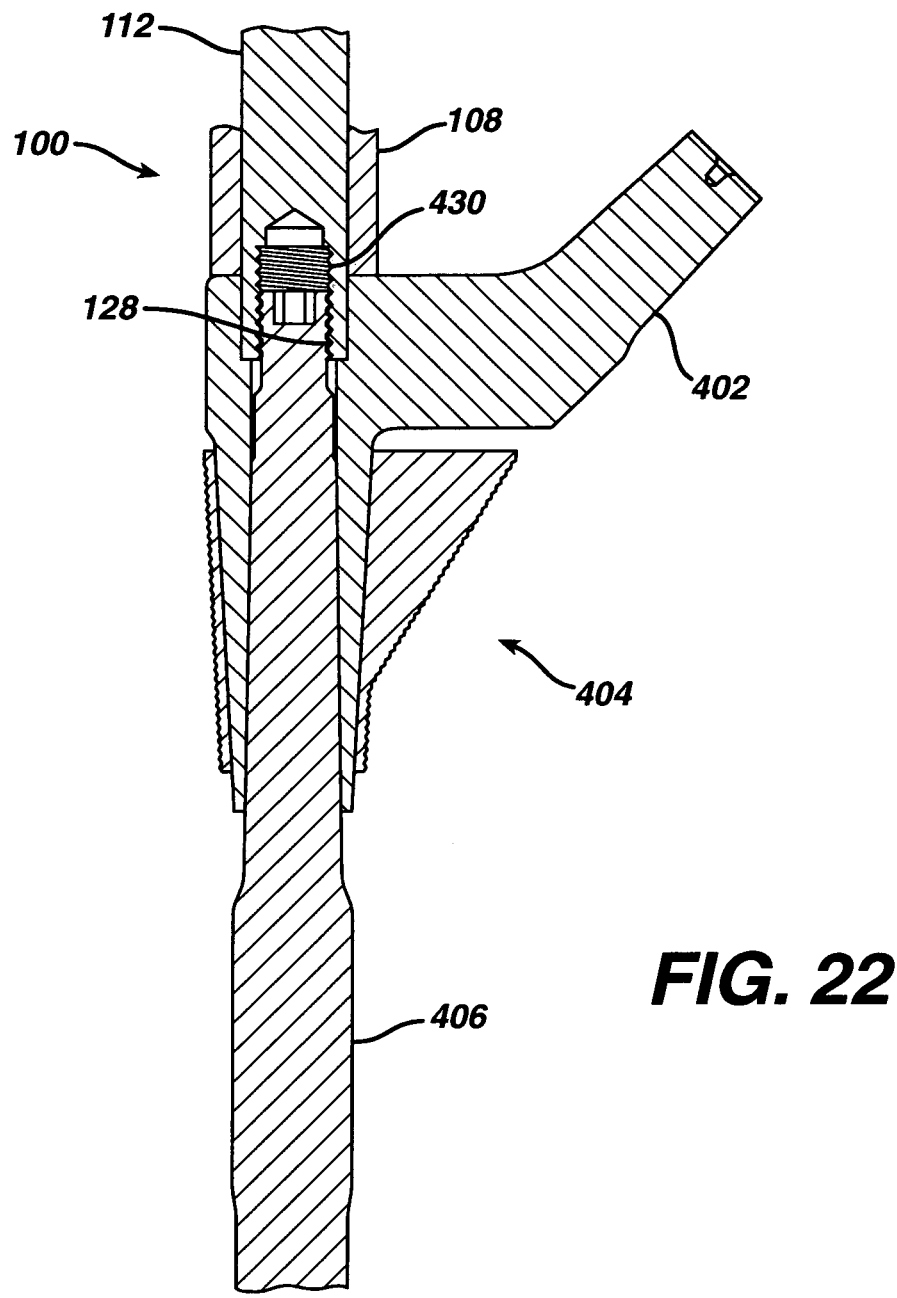
FIG. 22 is a partial enlarged view of the implant of FIG. 8 being assembled with the assembly tool of FIG. 2.

Referring now to FIGS. 21 and 22, the prosthesis 404 is shown in connection with the assembly tool 100. Outer surface 124 of the first member 108 of the assembly tool 100 is placed against top surface 426 of the proximal body 402 of the prosthesis 404. The internal threads 128 of the second member 108 of the assembly tool 100 is threadably engaged with external threads 430 of the distal stem 406. After the prosthesis 404 has been assembled with the assembly tool 100, nut 423 shown in phantom is positioned on the external threads 430 of the distal stem 406.

Referring again to FIG. 13, the assembly tool 100 is shown in greater detail. While the first member 108 and the second member 112 may be made of a one-piece or unitary construction, it should be appreciated that the first member 108 and the second member 112 may be made of multiple components or may be modular. For example, and referring to FIG. 13, the first member 108 may include a sleeve portion 140, having a lower sleeve 186 as well as an upper sleeve 188.

Figure 13:
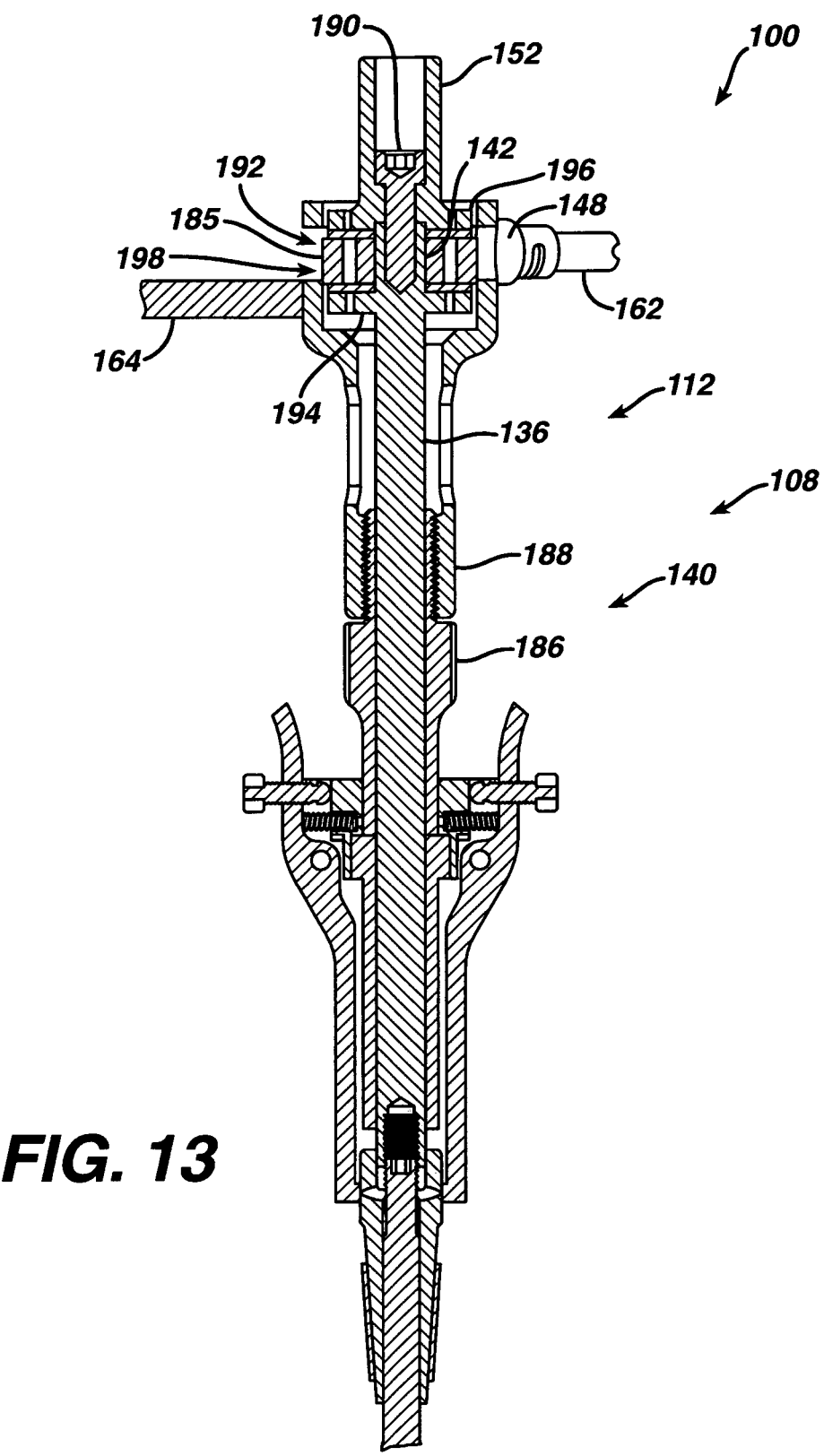
FIG. 13 is a cross-sectional plan view of the assembly tool of FIG. 2 showing the implant of FIG. 8 being disassembled.
Figure 14:
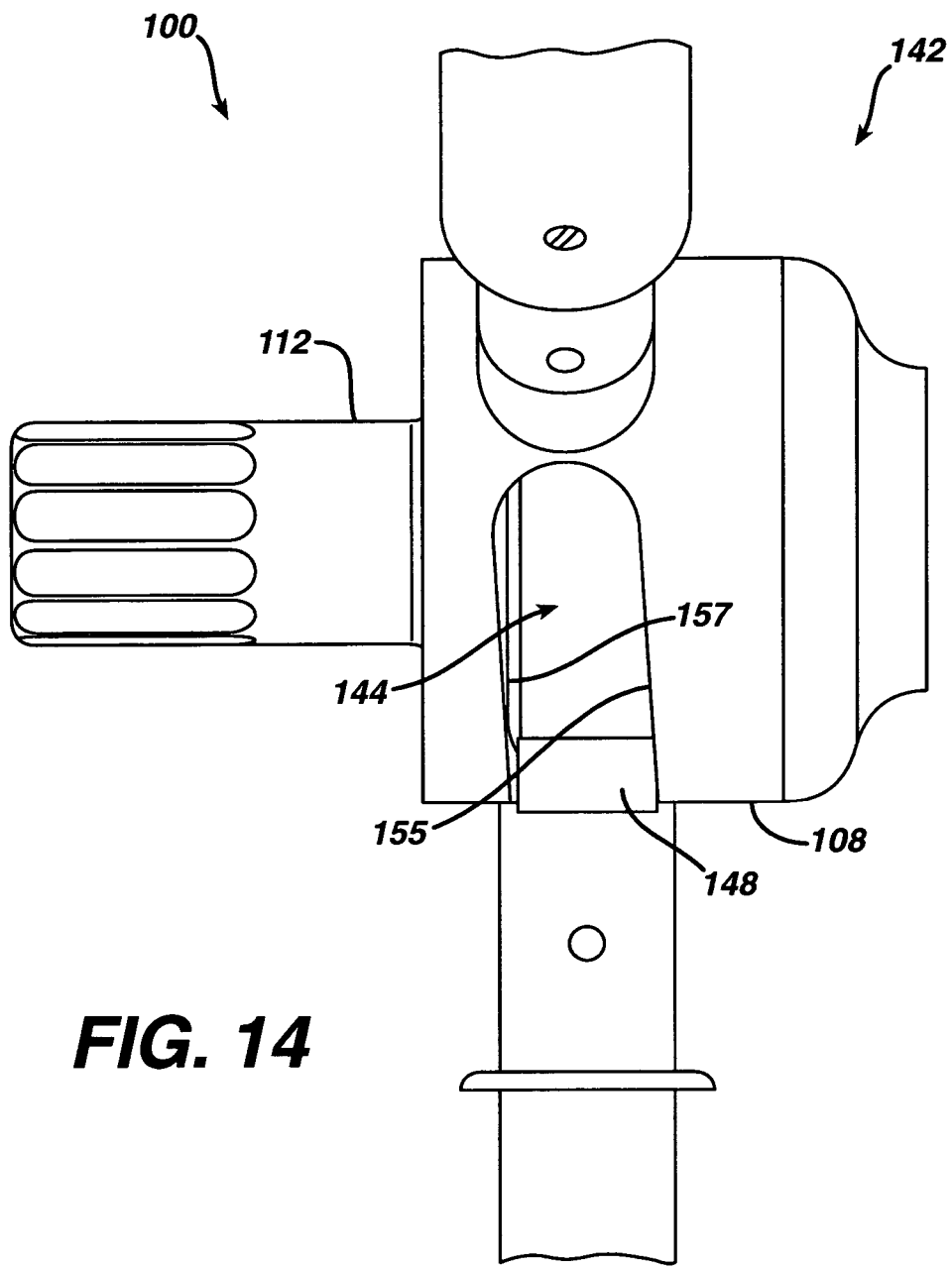
FIG. 14 is a partial enlarged plan view of the assembly tool of FIG. 2 showing the ramp actuation mechanism in greater detail.
Figure 15:
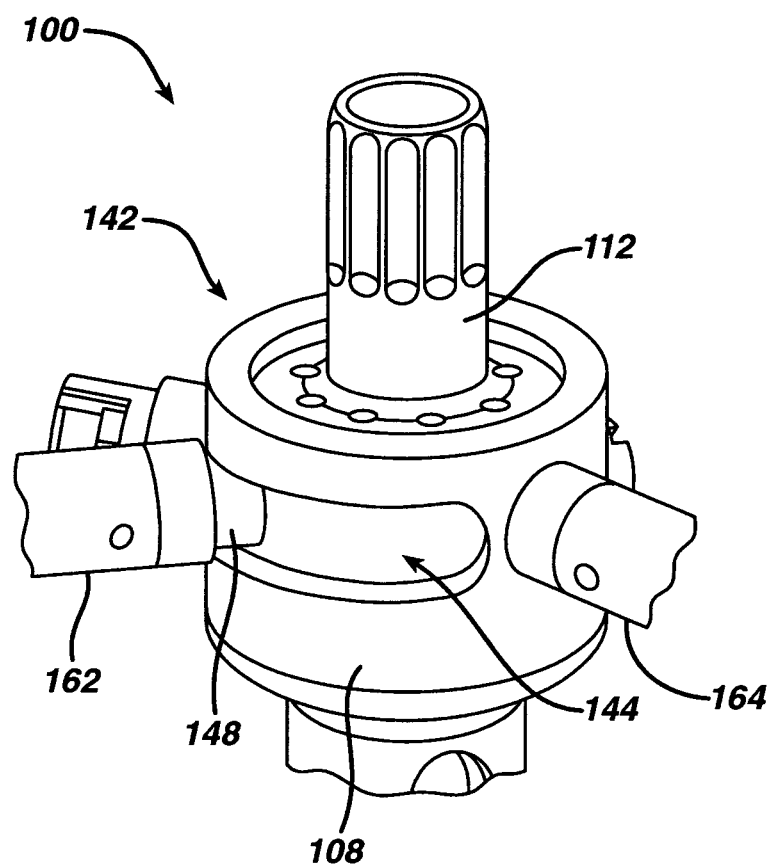
FIG. 15 is a partial enlarged perspective view of the assembly tool of FIG. 2 showing the ramp actuation mechanism in greater detail.

The lower sleeve 186 may be connected to the upper sleeve 188 in any suitable manner, for example, by welding, by press fit, or as shown in FIG. 13, by being threadably connected. The first member 108 may also include a third component in the form of the first member handle 164. The first member handle 164 may be removably connected to the upper sleeve 188 by, for example, a bayonet connection such as that described in FIGS. 18 and 19 herein.

Similarly, the second member 112 may be made of a modular or multi-piece construction. For example, the second member 112 may include a rod portion 136 removably connected to a cap 152. The rod portion 136 may be secured to the cap 152 in any suitable fashion. For example, the cap 152 may be welded to the rod portion 136, or be press fitted thereto. Alternatively, and as shown in FIG. 13, the rod portion 136 may be threadably connected to the cap 152 by means of a screw 190 threadably secured to the rod portion 136 and trapping the cap 152 therebetween. As shown in FIG. 13, the cap 152 and the rod portion 136 cooperate to form a spool 192 therebetween. The spool 192 includes a first retaining portion 194 extending from the rod portion 136 and a spaced-apart and parallel second restraining portion 196. A central portion 198 is positioned between the first restraining portion 194 and the second restraining portion 196.

Continuing to refer to FIG. 13, the second member 112 of the assembly tool 100 further includes a ring 185 rotatably positioned about the central portion 198 of the rod portion 136. The pin 148 is retainably connected to the ring 185. The handle 162 is fixedly secured to the ring 185 by, for example, a press fit or fitted connection similar to the connection of FIGS. 18 and 19.

Figure 23:
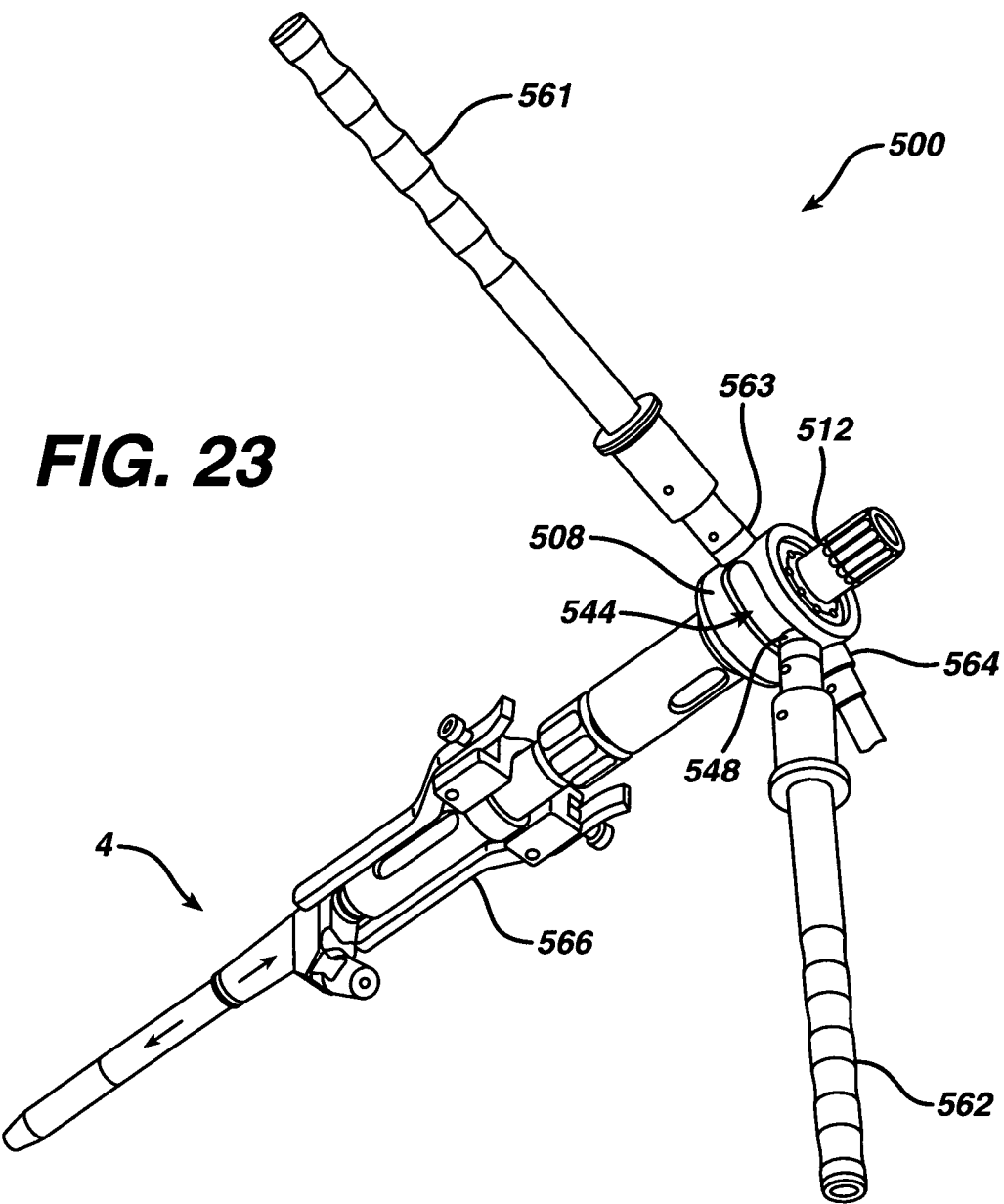
FIG. 23 is a perspective view of the implant of FIG. 4 being disassembled with the assembly tool of FIG. 2.
Figure 24:
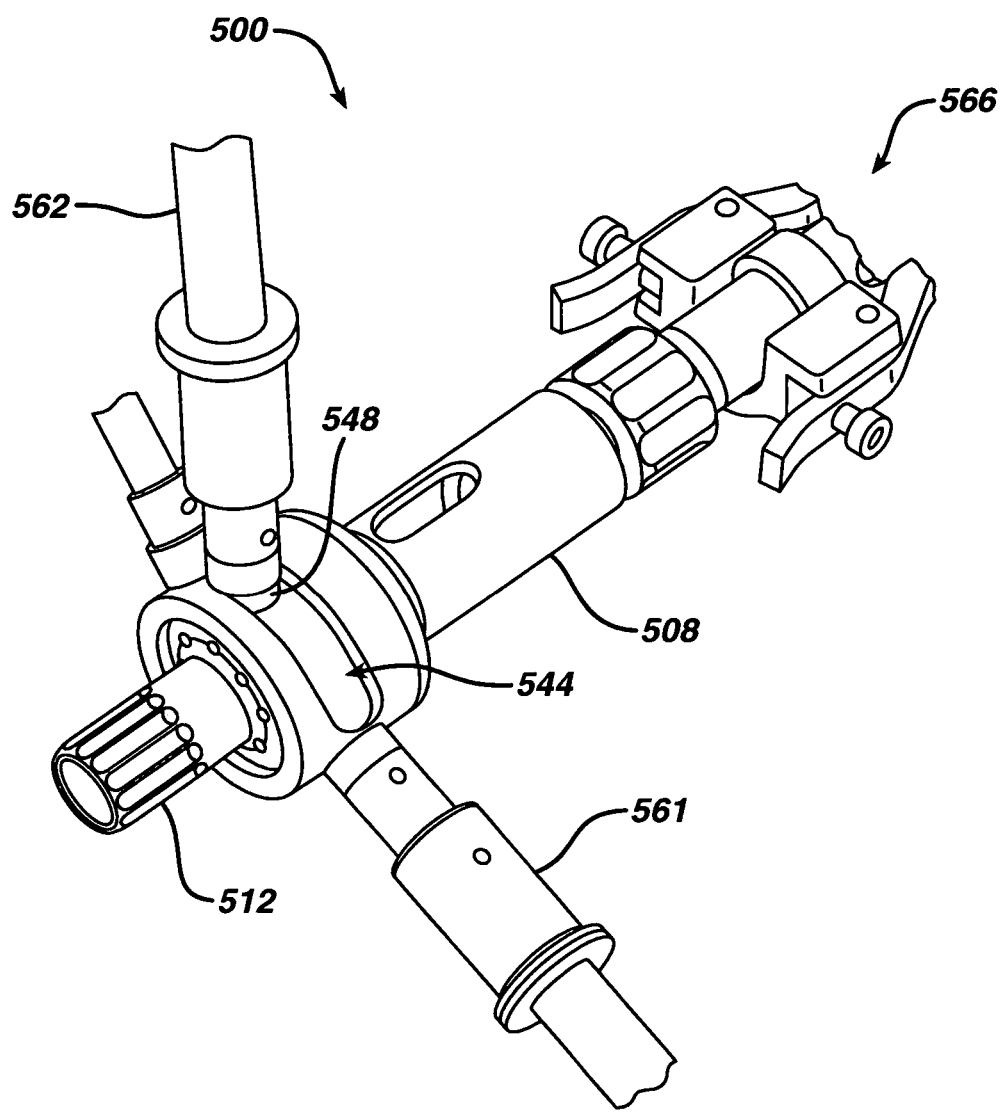
FIG. 24 is a partial enlarged perspective view of the assembly tool of FIG. 2 including the adaptor for use in disassembly.
Figure 25:
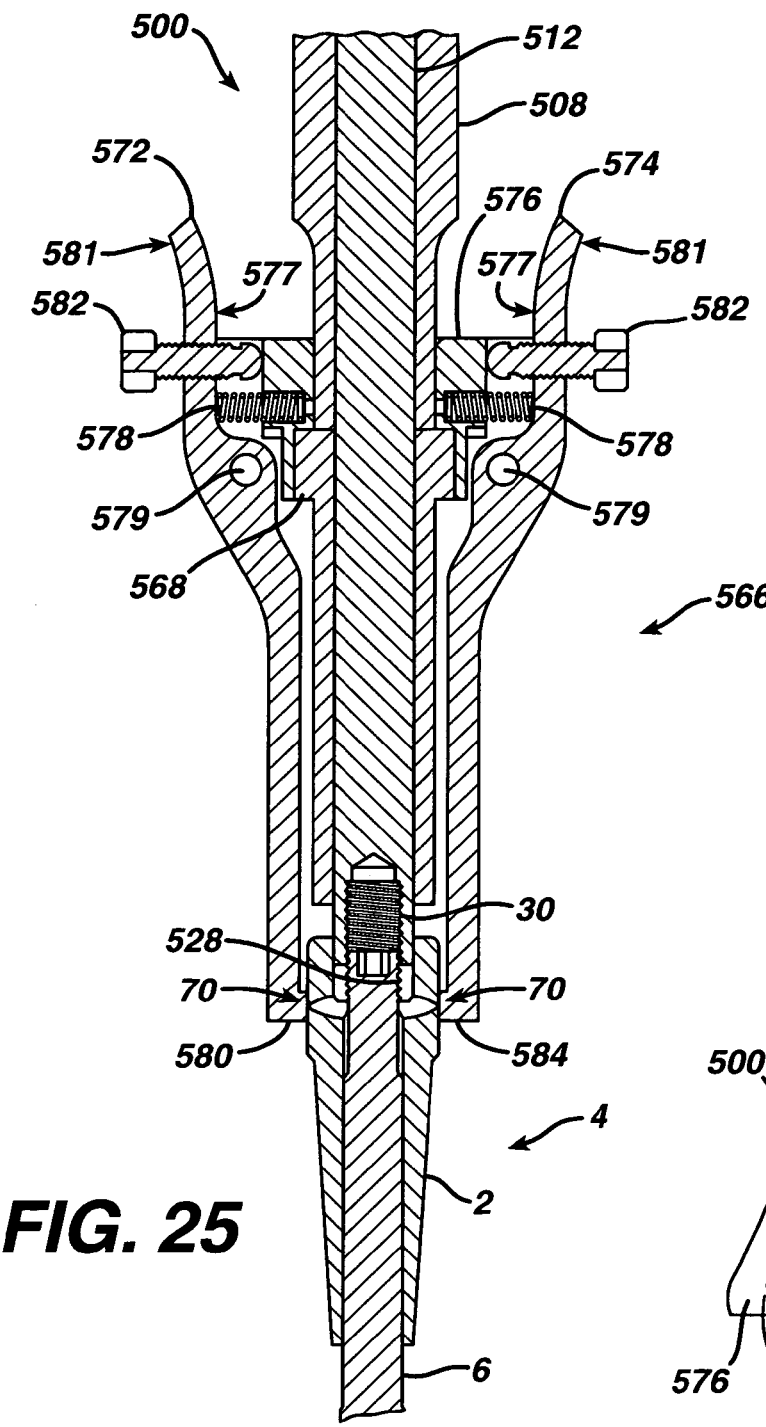
FIG. 25 is a partial cross-sectional plan view of the assembly tool of FIG. 2 showing the implant of FIG. 4 being disassembled and showing the removable disassembly component in position on the assembly tool.

Referring now to FIGS. 23, 24, and 25, assembly tool 500 is shown for use in disassembling the prosthesis 4. The assembly tool 500 is similar to the assembly tool 100 and in fact includes all the components of the assembly tool 100 plus a third member 566 for use in disassembling the prosthesis 4. The assembly tool 500 thus includes a first member 508 identical to the first member 108 as well as a second member 512 identical to the second member 112 of the assembly tool 100 (see FIG. 13).

The assembly tool 500 includes an actuating arm 562 identical to the actuating arm 162 of the tool assembly 100. The assembly tool 500 further includes a restraining arm 561 identical to the restraining arm 162 of assembly tool 100, except that the arm extension 161 of the restraining arm 162 is moved from first arm stem 564 to second arm stem 563. The assembly tool 500 includes a slot 544 identical to the slot 144 of the assembly tool 100. Pin 548, identical to pin 148 of the assembly tool 100, slidably fits within the slot 548.

Referring now to FIG. 25, the third member 566 is shown in greater detail. The third member 566 includes a collar 576 which is slidably fitted over the first member shoulder 568. First arm 572 and second arm 574 are pivotally mounted to the collar 576 by pivot pins 579. The arms 572 and 574 are urged in the direction of arrows 577 by springs 578 positioned between the arms 572 and 574 and the collar 576. Screws 582 are threadably secured to the arms 572 and 574 to limit the movement of the upper portion of the arms 572 and 574 toward the first member 508. First location pin 580 and second location pin 584 are positioned on the first arm 572 and the second arm 574, respectively, for engagement with holes 70 in the proximal body 2 of the prosthesis 4.

When disassembling the prosthesis for utilizing the assembly tool 500, the location pins 580 and 582 are engaged in the holes 70 of the proximal body 2 of the prosthesis 4. Internal threads 528 of the second member 508 are then threadably engaged into the external threads 30 of the distal stem 6 of the prosthesis 4. The second member 512 is then continually tightened until the second member 512 is finger tight to the distal stem 6. The pins 580 and 584 are moved from the proximal body 2 by first moving the arms 572 and 574 in the direction of arrows 581 by means of the operator's fingers. When in position the arms 572 and 574 are released so that the pins 580 and 584 may be properly engaged in the holes 70 of the proximal body 2 of the prosthesis 4.

Figure 26:
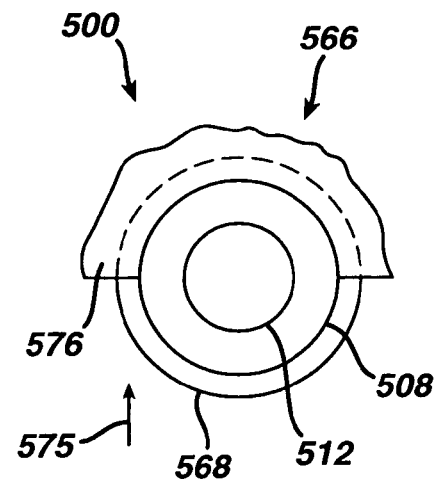
FIG. 26 is a partial top view of the assembly tool of FIG. 2 showing the removable disassembly component in position on the assembly tool.

Referring now to FIG. 26, the collar 576 of the third member 566 is shown in position on the first member 508. The third member 566 is assembled to the first member 508 by moving the third member 566 in the direction of arrow 575.

Figure 27:
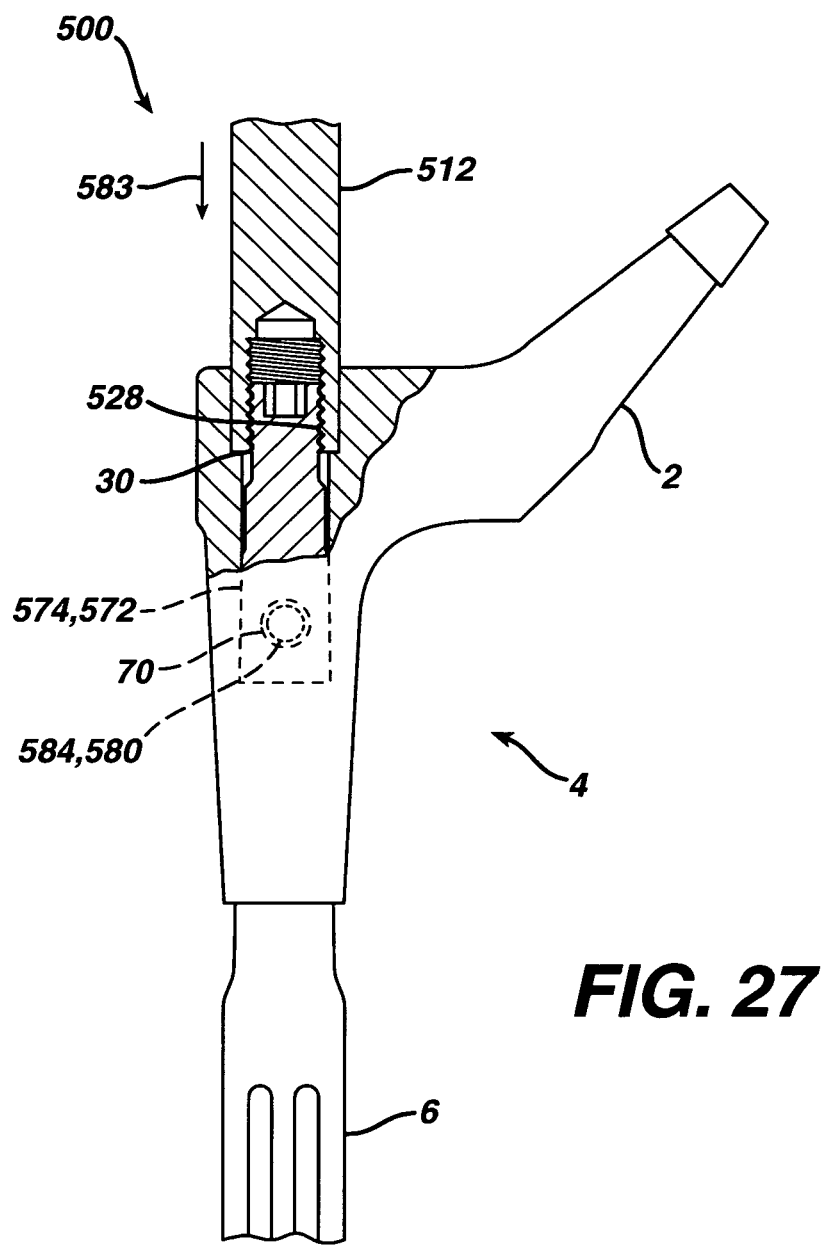
FIG. 27 is a partial enlarged plan view of the implant of FIG. 4 being disassembled with the assembly tool of FIG. 2.

Referring now to FIG. 27, the assembly tool 500 is shown for use with the prosthesis 4 to disassemble the proximal body 2 from the distal stem 6. The pins 580 and 584 of the arms 572 and 574 of the third member 566 are engaged in holes 70 of the proximal body 2 of the prosthesis 4. The internal threads 528 of the second member 512 are threadably engaged with the external threads 30 of the distal stem 6. The second member 512 is then moved downwardly in the direction of arrow 583, thereby separating the distal stem 6 from the proximal body 2.

Figure 28:
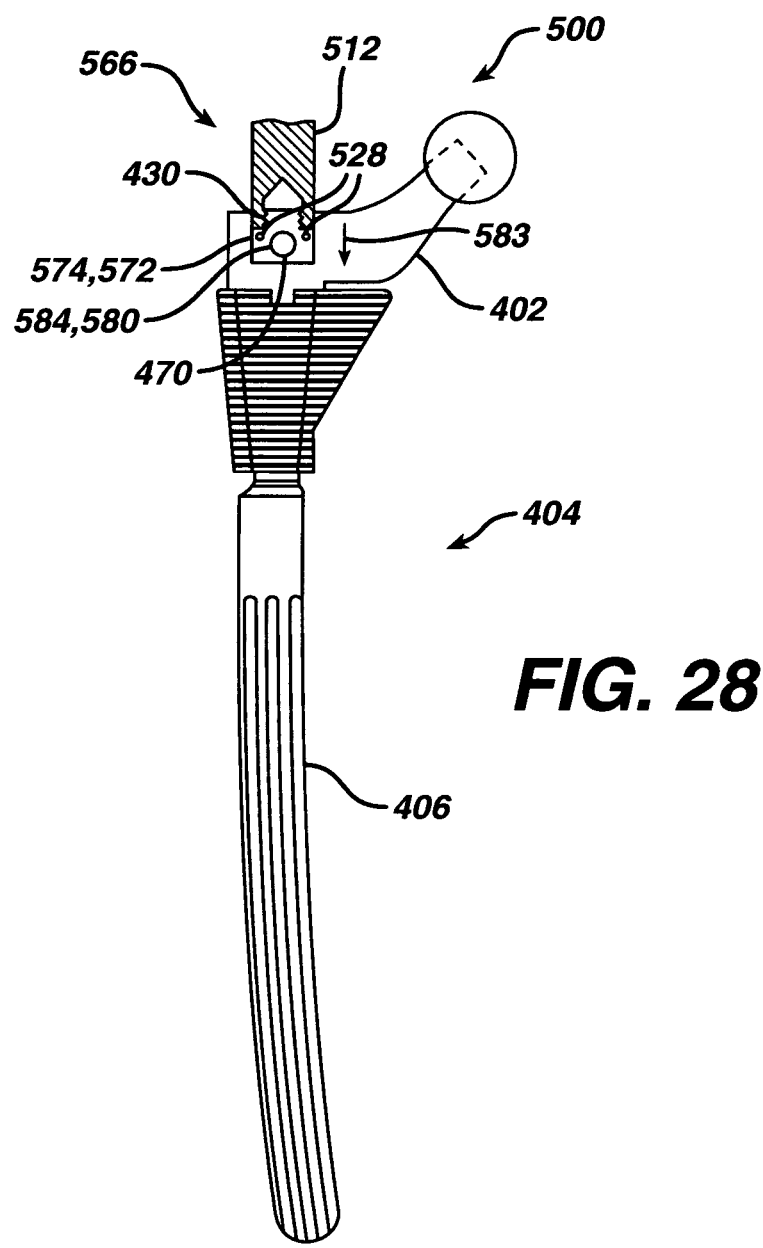
FIG. 28 is a partial enlarged plan view of the implant of FIG. 8 being disassembled with the assembly tool of FIG. 2.

Referring now to FIG. 28, the assembly tool 500 is shown in engagement with the prosthesis 404 to remove the distal stem 406 of the prosthesis 404 from the proximal body 402. The pins 580 and 584 of the arms 572 and 574 of the third member 566 are engaged in holes 470 of the proximal body 402 of the prosthesis 404. The internal threads 528 of the second member 512 are threadably engaged with the external threads 430 of the distal stem 406 of the prosthesis 404. The second member 512 is then moved in the direction of arrow 583 with respect to the proximal body 402 of the prosthesis 404 thereby separating the distal stem 406 from the proximal body 402 of the stem 404.

Figure 29:
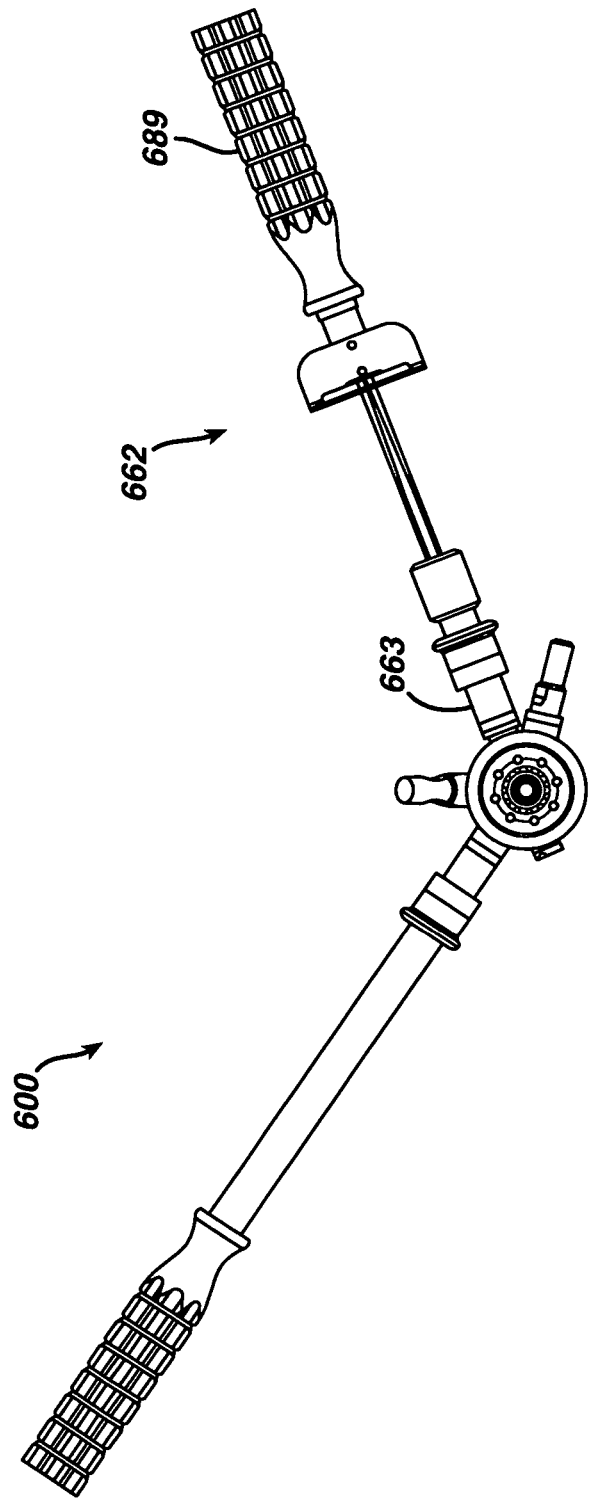
FIG. 29 is a plan view of another embodiment of the present invention in the form of an assembly tool including a torque wrench for measuring the torque applied to the modular implant.

Referring now to FIG. 29, another embodiment of the present invention is shown as assembly tool 600. Assembly tool 600 is similar to assembly tool 100 or assembly tool 500 of FIG. 2 and FIG. 24, respectively, except that articulating arm 662 of the assembly tool 600 is different than the articulating arm 562 of the assembly tool 500 in that the articulating arm 662 includes a torque wrench 689 extending from the arm stem 663. The torque wrench 689 serves to provide a reading of the torque applied by the assembly tool 600. It should be appreciated that the torque wrench 689 may be of a type for recording or reading the applied torque or may be a torque wrench which has a break away or clicking torque at a particular value. Such a torque limiting wrench may provide for a accurate torque to be applied by the assembly tool 600. It should be appreciated that a thrust washer or other force transducer may be positioned in the first member or the second member to monitor the force asserted by the assembly tool.

Referring again to FIG. 10, another embodiment of the present invention is shown as kit 700. Kit 700 includes the assembly tool 100 as well as the prosthesis 4. The assembly tool 100 and the prosthesis 4 form a kit. The kit may be provided with the prosthesis 4 assembled or with the prosthesis 4 disassembled including both the proximal body 2 and the distal stem 6.

Assembly tools 1, 100 and 500 as shown in FIGS. 1, 2 and 24 respectively, may be made of any suitable material and may, for example, be made of a metal. If made of metal, preferably the assembly tool is made of a sterilizable material. The assembly tools 100 and 500 may be made of components of, for example, cobalt chromium alloy, stainless steel alloy, or a titanium alloy. Articulating surfaces of the assembly tool may be surface hardened by processes such as flame hardening.

Referring now to FIG. 30, another embodiment of the present invention is shown as surgical method 800. The method 800 includes a first step 802 of providing a prosthesis including a first component and a second component removably attached to the first component. The surgical procedure 800 also includes a second step 804 of providing an instrument having a first member and a second member rotatably movable with respect to the first member in a plane perpendicular with the first member, the first member cooperable with the second component and the second member cooperable with the second component.

The method 800 may further include a third step 806 of assembling the first component to the second component and a fourth step 808 of connecting the first member of the tool to the first component. The method 800 may further include a fifth step 810 of connecting the second member of the tool to the second component and a sixth step 812 of rotating the first member of the tool with respect to the second member of the tool to secure the second component to the first component.

Although the present invention and its advantages have been described in detail, it should be understood that various changes, substitutions, and alterations can be made therein without departing from the spirit and scope of the present invention as defined by the appended claims.

We claim:

1. An assembly tool for assembly of a proximal body component of a prosthesis to a distal stem component of the prosthesis for use in joint arthroplasty, the tool comprising:
   a tube component defining a longitudinal opening therethrough and including:
      a tube component handle located at an end thereof and configured for manually grasping to hold the tube component in a fixed position relative to the distal stem component; and
      a tube-prosthesis contact surface located at an opposite end relative to the tube component handle, wherein the tube component contacts the proximal body component at the tube-prosthesis contact surface;
   a rod component including:
      a sliding portion movably received within the longitudinal opening of the tube component for rotation and translation relative to the tube component;
      a rod component handle located at an end of the rod component and configured for manually grasping to rotate the rod component relative to the tube component; and
      an operative portion located at an opposite end relative to the rod component handle and configured to operably engage the distal stem component such that the distal stem component translates relative to the proximal body component as the rod component translates relative to the tube component; and
   a relative motion feature defined between the tube component and the rod component, the relative motion feature converting torque applied to the rod component through the rod component handle into translation of the sliding portion of the rod component relative to the tube component.

2. The assembly tool of claim 1, wherein the rod component has a rod component longitudinal axis and the tube component has a tube component longitudinal axis, the rod component longitudinal axis and the tube component longitudinal axis being coincidental.

3. The assembly tool of claim 1, wherein the relative motion feature includes:
   a rod component relative motion threaded portion located on the rod component; and
   a tube component relative motion threaded portion located on the tube component for threadably engaging the rod component relative motion threaded portion.

4. The assembly tool of claim 3, wherein:
   the rod component relative motion threaded portion includes external threads on an outside surface of the rod component; and
   the tube component relative motion threaded portion includes internal threads on an inside surface of the tube component.

5. The assembly tool of claim 4, wherein:
the external threads are located at the end of the rod component adjacent to the rod component handle; and
the internal threads are located at the end of the tube component adjacent to the tube component handle.

6. The assembly tool of claim 3, wherein the rod component relative motion threaded portion has a first length and the tube component relative motion threaded portion has a second length, translation of the rod component relative to the tube component being limited by the relationship of the first length to the second length.

7. The assembly tool of claim 6, wherein the first length is different than the second length, a distance of translation of the rod component relative to the tube component being limited to the shorter of the first and second lengths.

8. The assembly tool of claim 1, wherein the relative motion feature includes:
the tube component further including a wall having an outer surface and an inner surface, the inner surface forming the longitudinal opening; and
the relative motion feature further including:
a slot formed in the wall of the tube component, extending from the outer surface to the inner surface, the slot slanting upwardly as it extends around the wall; and
a pin extending outwardly from the sliding portion of the rod component, the pin being sized and configured to extend through the slot and matingly slide within the slot.

9. The assembly tool of claim 8, wherein the relative motion feature further includes:
a second slot formed in the wall of the tube component, the second slot being positioned in the wall opposite the slot; and
a second pin extending outwardly from the sliding portion of the rod component, the second pin being positioned on the sliding portion opposite the pin, the second pin being sized and configured to extend through the second slot and matingly slide within the second slot while the pin extends through and matingly slides within the slot.

10. The assembly tool of claim 8, wherein the rod component has a two-piece construction including a spool having a central portion having first and second ends and having first and second restraining portions extending from the first and second ends, respectively, and including a ring contained within the spool and rotatable therewithin, the ring operably associated with the pin.

11. The assembly tool of claim 1, further comprising:
a disassembly member attachable to the rod component and the tube component to retain the rod component and the tube component in fixed position relative to one another.

12. The assembly tool of claim 11, wherein the disassembly member comprises at least one spring to retain the rod component and the tube component in fixed position relative to one another.

13. The assembly tool of claim 11, wherein the rod component includes a rod component groove to receive at least a portion of the disassembly member and the tube component includes a tube component groove to receive at least another portion of the disassembly member.

14. The assembly tool of claim 1, further comprising one of a displacement measuring device and a force measuring device for measuring the corresponding one of the displacement and force related to the relative motion of the distal stem component relative to the proximal body component.

15. A prosthetic joint arrangement for use in joint arthroplasty comprising:
a proximal body;
a distal stem for attachment to the proximal body; and
an assembly tool to attach the proximal body to the distal stem, the assembly tool including:
a tube component defining a longitudinal opening therethrough and including:
a tube component handle located at an end thereof and configured for manually grasping to hold the tube component in a fixed position relative to the distal stem component; and
a tube-prosthesis contact surface located at an opposite end relative to the tube component handle, wherein the tube component contacts the proximal body component at the tube-prosthesis contact surface;
a rod component including:
a sliding portion movably received within the longitudinal opening of the tube component for rotation and translation relative to the tube component;
a rod component handle located at an end of the rod component and configured for manually gasping to rotate the rod component relative to the tube component; and
an operative portion located at an opposite end relative to the rod component handle and configured to operably engage the distal stem component such that the distal stem component translates relative to the proximal body component as the rod component translates relative to the tube component; and
a relative motion feature defined between the tube component and the rod component, the relative motion feature converting torque applied to the rod component through the rod component handle into translation of the sliding portion of the rod component relative to the tube component.

16. The assembly tool of claim 15, wherein the rod component has a rod component longitudinal axis and the tube component has a tube component longitudinal axis, the rod component longitudinal axis and the tube component longitudinal axis being coincidental.

17. The assembly tool of claim 15, wherein the relative motion feature includes:
a rod component relative motion threaded portion located on the rod component; and
a tube component relative motion threaded portion located on the tube component for threadably engaging the rod component relative motion threaded portion.

18. The assembly tool of claim 17, wherein:
the rod component relative motion threaded portion includes external threads on an outside surface of the rod component; and
the tube component relative motion threaded portion includes internal threads on an inside surface of the tube component.

19. The assembly tool of claim 18, wherein:
the external threads are located at the end of the rod component adjacent to the rod component handle; and
the internal threads are located at the end of the tube component adjacent to the tube component handle.

20. The assembly tool of claim 17, wherein the rod component relative motion threaded portion has a first length and the tube component relative motion threaded portion has a second length, translation of the rod component relative to the tube component being limited by the relationship of the first length to the second length.

21. The assembly tool of claim 20, wherein the first length is different than the second length, a distance of translation of the rod component relative to the tube component being limited to the shorter of the first and second lengths.

22. The assembly tool of claim 15, wherein the relative motion feature includes:
   the tube component further including a wall having an outer surface and an inner surface, the inner surface forming the longitudinal opening; and
   the relative motion feature further including:
      a slot formed in the wall of the tube component, extending from the outer surface to the inner surface, the slot slanting upwardly as it extends around the wall; and
      a pin extending outwardly from the sliding portion of the rod component, the pin being sized and configured to extend through the slot and matingly slide within the slot.

23. The assembly tool of claim 22, wherein the relative motion feature further includes:
   a second slot formed in the wall of the tube component, the second slot being positioned in the wall opposite the slot; and
   a second pin extending outwardly from the sliding portion of the rod component, the second pin being positioned on the sliding portion opposite the pin, the second pin being sized and configured to extend through the second slot and matingly slide within the second slot while the pin extends through and matingly slides within the slot.

24. The assembly tool of claim 22, wherein the rod component has a two-piece construction including a spool having a central portion having first and second ends and having first and second restraining portions extending from the first and second ends, respectively, and including a ring contained within the spool and rotatable therewithin, the ring operably associated with the pin.

25. The assembly tool of claim 15, further comprising:
   a disassembly member attachable to the rod component and the tube component to retain the rod component and the tube component in fixed position relative to one another.

26. The assembly tool of claim 25, wherein the disassembly member comprises at least one spring to retain the rod component and the tube component in fixed position relative to one another.

27. The assembly tool of claim 25, wherein the rod component includes a rod component groove to receive at least a portion of the disassembly member and the tube component includes a tube component groove to receive at least another portion of the disassembly member.

* * * * *